US008623815B2

(12) United States Patent
Berthoux et al.

(10) Patent No.: US 8,623,815 B2
(45) Date of Patent: Jan. 7, 2014

(54) TRIM5ALPHA MUTANTS AND USES THEREOF

(75) Inventors: Lionel Berthoux, Trois-Rivières (CA); Amélie Bouchard, Trois-Rivières (CA); Quang Toan Pham, Montréal (CA)

(73) Assignee: Université du Québec à Trois-Rivirères, Trois-Rivières (CA)

( * ) Notice: Subject to any disclaimer, the term of this patent is extended or adjusted under 35 U.S.C. 154(b) by 0 days.

(21) Appl. No.: 13/511,500

(22) PCT Filed: Nov. 19, 2010

(86) PCT No.: PCT/CA2010/001822
§ 371 (c)(1),
(2), (4) Date: Jul. 11, 2012

(87) PCT Pub. No.: WO2011/060534
PCT Pub. Date: May 26, 2011

(65) Prior Publication Data
US 2012/0270773 A1    Oct. 25, 2012

Related U.S. Application Data

(60) Provisional application No. 61/263,594, filed on Nov. 23, 2009.

(51) Int. Cl.
| | | |
|---|---|---|
| C07K 14/47 | (2006.01) |
| A61K 38/17 | (2006.01) |
| A61P 31/18 | (2006.01) |
| C12N 15/12 | (2006.01) |
| C12Q 1/68 | (2006.01) |
| G01N 33/48 | (2006.01) |
| G01N 33/68 | (2006.01) |
| A61K 38/00 | (2006.01) |
| C07K 14/005 | (2006.01) |
| C07K 7/02 | (2006.01) |

(52) U.S. Cl.
USPC .......................................... 514/3.7; 514/3.8

(58) Field of Classification Search
CPC ...... C07K 14/005; A61K 38/17; A61P 31/18; C12N 15/12; C12Q 1/68; G01N 33/48; G01N 33/53
USPC .................................... 514/3.7, 3.8
See application file for complete search history.

(56) References Cited

U.S. PATENT DOCUMENTS

2007/0141679 A1* 6/2007 Sodroski et al. ............. 435/91.1

FOREIGN PATENT DOCUMENTS

| CA | 2010001822 | 3/2011 |
| WO | WO2005081911 | 9/2005 |

OTHER PUBLICATIONS

Stremlau, M., et al., "Species-Specific Variation in the B30.2(SPRY) Domain of TRIM5alpha Determines the Potency of Human Immunodeficiency Virus Restriction," J. Virol. 79(5):3139-3145 (2005).*
Chan et al., "Interpreting missense mutations in human TRIM5alpha by computational methods," BMC Res. Notes 1:116-122 (2008).*
Diaz-Griffero, et al. "A human TRIM5α B30.2/SPRY domain mutant gains the ability to restrict and prematurely uncoat B-tropic murine leukemia virus," Virol. 378:233-242 (2008).*
Li et al., "Removal of Arginine 322 allows human TRIM5α to bind human immunodeficiency virus capsids and to restrict infection," J. Virol. 80(14):6738-6744 (2006)).*
Yap et al., "A single amino acid change in the SPRY domain of human leads to HIV-1 restriction," Curr. Biol. 15:73-78 (2005).*
Javanbakht et al., Effects of human TRIM5a polymorphisms on antiretroviral function and susceptibility to human immunodeficience virus infection, Virology 2006, vol. 354; pp. 15-27.
Li et al., Removal of argininine 332 allows human TRIM5a to bind human immunodeficiency virus capsids and to restrict infection, Journal of Virology 2006, vol. 80 (14) pp. 6738-6744.
Maillard et al., Interfering residues narrow the spectrum of MLV restriction by human TRIM5a, PLoS Pathogens, 2007, vol. 3, issue 12, pp. 2052-2062.
Newman et al., A brief history of TRIM5a, Aids Reviews, 2007, vol. 9, pp. 114-125.
Speelmon et al., Genetic association of the antiviral restriction factor TRIM5a with human immunodeficiency virus type 1 infection, Journal of Virology 2006, vol. 80(5) pp. 2463-2471.
Stremlau et al., The cytoplasmic body component TRIM5a restricts HIV-1 infection in Old World Monkeys, Letters to Nature 2004, vol. 427, pp. 848-853.
Stremlau et al., Species-specific variation in the B30.2 (SPRY) domain of TRIM5a determines the potency of human immunodeficiency virus restriction, Journal of Virology 2005, vol. 79 (5) pp. 3139-3145.
Yap et al., A single amino acid change in the SPRY domain of human TRIM5a leads to HIV restriction, Current Biology 2005, vol. 15 pp. 73-78.

* cited by examiner

*Primary Examiner* — Cecilia J Tsang
*Assistant Examiner* — Kristina M Hellman
(74) *Attorney, Agent, or Firm* — Goudreau Gage Dubuc; S. Serge Shahinian; Alain Dumont

(57) ABSTRACT

New mutant forms of TRIM5α comprising one or more mutations at amino acid positions corresponding to amino acids 324, 328, 330, 333, 335, 336 and/or 337 of wild-type human TRIM5α and which inhibit retrovirus replication are described. These mutants may be used, for example, in gene therapy applications for the prevention and/or treatment of retroviral infection and associated conditions, such as HIV-1 infection and AIDS.

11 Claims, 20 Drawing Sheets

Nucleotide (SEQ ID NO: 23) and amino acid (SEQ ID NO: 24) sequence of human TRIM5α

```
atg gct tct gga atc ctg gtt aat gta aag gag gag gtg acc tgc ccc      48
Met Ala Ser Gly Ile Leu Val Asn Val Lys Glu Glu Val Thr Cys Pro
1               5                   10                  15
atc tgc ctg gaa ctc ctg aca caa ccc ctg agc ctg gac tgc ggc cac      96
Ile Cys Leu Glu Leu Leu Thr Gln Pro Leu Ser Leu Asp Cys Gly His
                20                  25                  30
agc ttc tgc caa gca tgc ctc act gca aac cac aag aag tcc atg cta     144
Ser Phe Cys Gln Ala Cys Leu Thr Ala Asn His Lys Lys Ser Met Leu
            35                  40                  45
gac aaa gga gag agc agc tgc cct gtg tgc cgg atc agt tac cag cct     192
Asp Lys Gly Glu Ser Ser Cys Pro Val Cys Arg Ile Ser Tyr Gln Pro
        50                  55                  60
gag aac ata cgg cct aat cgg cat gta gcc aac tta gtg gag aag ctc     240
Glu Asn Ile Arg Pro Asn Arg His Val Ala Asn Leu Val Glu Lys Leu
65                  70                  75                  80
agg gag gtc aag ttg agc cca gag ggg cag aaa gtt gat cat tgt gca     288
Arg Glu Val Lys Leu Ser Pro Glu Gly Gln Lys Val Asp His Cys Ala
                85                  90                  95
cgc cat gga gag aaa ctt cta ctc ttc tgt cag gag gac ggg aag gtc     336
Arg His Gly Glu Lys Leu Leu Leu Phe Cys Gln Glu Asp Gly Lys Val
            100                 105                 110
att tgc tgg ctt tgt gag cgg tct cag gag cac cgt ggt cac cac acg     384
Ile Cys Trp Leu Cys Glu Arg Ser Gln Glu His Arg Gly His His Thr
        115                 120                 125
ttc ccc aca gag gag gtt gcc cag gag tac caa gtg aag ctc cag gca     432
Phe Pro Thr Glu Glu Val Ala Gln Glu Tyr Gln Val Lys Leu Gln Ala
130                 135                 140
gct ctg gag atg ctg agg cag aag cag cag gaa gct gaa gag ttg gaa     480
Ala Leu Glu Met Leu Arg Gln Lys Gln Gln Glu Ala Glu Glu Leu Glu
145                 150                 155                 160
gct gac atc aga gaa gag aaa gct tcc tgg aag act caa ata cag tat     528
Ala Asp Ile Arg Glu Glu Lys Ala Ser Trp Lys Thr Gln Ile Gln Tyr
                165                 170                 175
gac aaa acc aac gtc ttg gca gat ttt cag caa ctg aga gac atc ctg     576
Asp Lys Thr Asn Val Leu Ala Asp Phe Gln Gln Leu Arg Asp Ile Leu
            180                 185                 190
gac tgg gag gag agc aat gag ctg caa aac ctg gag aag gag gag gaa     624
Asp Trp Glu Glu Ser Asn Glu Leu Gln Asn Leu Glu Lys Glu Glu Glu
        195                 200                 205
gac att ctg aaa agc ctt acg aac tct gaa act gag atg gtg cag cag     672
Asp Ile Leu Lys Ser Leu Thr Asn Ser Glu Thr Glu Met Val Gln Gln
210                 215                 220
acc cag tcc ctg aga gag ctc atc tca gat ctg gag cat cgg ctg cag     720
Thr Gln Ser Leu Arg Glu Leu Ile Ser Asp Leu Glu His Arg Leu Gln
225                 230                 235                 240
ggg tca gtg atg gag ctg ctt cag ggt gtg gat ggc gtc ata aaa agg     768
Gly Ser Val Met Glu Leu Leu Gln Gly Val Asp Gly Val Ile Lys Arg
                245                 250                 255
acg gag aac gtg acc ttg aag aag cca gaa act ttt cca aaa aat caa     816
Thr Glu Asn Val Thr Leu Lys Lys Pro Glu Thr Phe Pro Lys Asn Gln
            260                 265                 270
```

FIG. 6A

```
agg aga gtg ttt cga gct cct gat ctg aaa gga atg cta gaa gtg ttt    864
Arg Arg Val Phe Arg Ala Pro Asp Leu Lys Gly Met Leu Glu Val Phe
        275                 280                 285
aga gag ctg aca gat gtc cga cgc tac tgg gtt gat gtg aca gtg gct    912
Arg Glu Leu Thr Asp Val Arg Arg Tyr Trp Val Asp Val Thr Val Ala
        290                 295                 300
cca aac aac att tca tgt gct gtc att tct gaa gat aag aga caa gtg    960
Pro Asn Asn Ile Ser Cys Ala Val Ile Ser Glu Asp Lys Arg Gln Val
305                 310                 315                 320
agc tct ccg aaa cca cag ata ata tat ggg gca cga ggg aca aga tac   1008
Ser Ser Pro Lys Pro Gln Ile Ile Tyr Gly Ala Arg Gly Thr Arg Tyr
                325                 330                 335
cag aca ttt gtg aat ttc aat tat tgt act ggc atc ctg ggc tct caa   1056
Gln Thr Phe Val Asn Phe Asn Tyr Cys Thr Gly Ile Leu Gly Ser Gln
            340                 345                 350
agt atc aca tca ggg aaa cat tac tgg gag gta gac gtg tcc aag aaa   1104
Ser Ile Thr Ser Gly Lys His Tyr Trp Glu Val Asp Val Ser Lys Lys
        355                 360                 365
act gct tgg atc ctg ggg gta tgt gct ggc ttc caa cct gat gca atg   1152
Thr Ala Trp Ile Leu Gly Val Cys Ala Gly Phe Gln Pro Asp Ala Met
    370                 375                 380
tgt aat att gaa aaa aat gaa aat tat caa cct aaa tac ggc tac tgg   1200
Cys Asn Ile Glu Lys Asn Glu Asn Tyr Gln Pro Lys Tyr Gly Tyr Trp
385                 390                 395                 400
gtt ata ggg tta gag gaa gga gtt aaa tgt agt gct ttc cag gat agt   1248
Val Ile Gly Leu Glu Glu Gly Val Lys Cys Ser Ala Phe Gln Asp Ser
                405                 410                 415
tcc ttc cat act cct tct gtt cct ttc att gtg ccc ctc tct gtg att   1296
Ser Phe His Thr Pro Ser Val Pro Phe Ile Val Pro Leu Ser Val Ile
            420                 425                 430
att tgt cct gat cgt gtt gga gtt ttc cta gac tat gag gct gc act    1344
Ile Cys Pro Asp Arg Val Gly Val Phe Leu Asp Tyr Glu Ala Cys Thr
        435                 440                 445
gtc tca ttc ttc aat atc aca aac cat gga ttt ctc atc tat aag ttt   1392
Val Ser Phe Phe Asn Ile Thr Asn His Gly Phe Leu Ile Tyr Lys Phe
    450                 455                 460
tct cac tgt tct ttt tct cag cct gta ttt cca tat tta aat cct aga   1440
Ser His Cys Ser Phe Ser Gln Pro Val Phe Pro Tyr Leu Asn Pro Arg
465                 470                 475                 480
aaa tgt gga gtc ccc atg act ctg tgc tca cca agc tct tga            1482
Lys Cys Gly Val Pro Met Thr Leu Cys Ser Pro Ser Ser
                485                 490
```

FIG. 6B

Amino acid sequence of human TRIM5α mutated at position 335 (SEQ ID NO: 25)

```
  1 masgilvnvk eevtcpicle lltqplsldc ghsfcqaclt anhkksmldk gesscpvcri
 61 syqpenirpn rhvanlvekl revklspegq kvdhcarhge klllfcqedg kvicwlcers
121 qehrghhtfp teevaqeyqv klqaalemlr qkqqeaeele adireekasw ktqiqydktn
181 vladfeqlrd ildweesnel qnlekeeedi lksltnsete mvqqtqslre lisdlehrlq
241 gsvmellqgv dgvikrtenv tlkkpetfpk nqrrvfrapd lkgmlevfre ltdvrrywvd
301 vtvapnnisc avisedkrqv sspkpqiiyg argtxyqtfv nfnyctgilg sqsitsgkhy
361 wevdvskkta wilgvcagfq pdamcniekn enyqpkygyw vigleegvkc safqdssfht
421 psvpfivpls viicpdrvgv fldyeactvs ffnitnhgfl iykfshcsfs qpvfpylnpr
481 kcgvpmtlcs pss
``` wherein x is D, E, G, K or is absent

FIG. 6C

Amino acid sequence of human TRIM5α mutated at positions 332 and 335 (SEQ ID NO: 26)

```
  1 masgilvnvk eevtcpicle lltqplsldc ghsfcqaclt anhkksmldk gesscpvcri
 61 syqpenirpn rhvanlvekl revklspegq kvdhcarhge klllfcqedg kvicwlcers
121 qehrghhtfp teevaqeyqv klqaalemlr qkqqeaeele adireekasw ktqiqydktn
181 vladfeqlrd ildweesnel qnlekeeedi lksltnsete mvqqtqslre lisdlehrlq
241 gsvmellqgv dgvikrtenv tlkkpetfpk nqrrvfrapd lkgmlevfre ltdvrrywvd
301 vtvapnnisc avisedkrqv sspkpqiiyg aggtxyqtfv nfnyctgilg sqsitsgkhy
361 wevdvskkta wilgvcagfq pdamcniekn enyqpkygyw vigleegvkc safqdssfht
421 psvpfivpls viicpdrvgv fldyeactvs ffnitnhgfl iykfshcsfs qpvfpylnpr
481 kcgvpmtlcs pss
``` wherein x is D, E, G, K or is absent

FIG. 6D

Amino acid sequence of human TRIM5α mutated at position 330 (SEQ ID NO: 30)

```
  1 masgilvnvk eevtcpicle lltqplsldc ghsfcqaclt anhkksmldk gesscpvcri
 61 syqpenirpn rhvanlvekl revklspegq kvdhcarhge klllfcqedg kvicwlcers
121 qehrghhtfp teevaqeyqv klqaalemlr qkqqeaeele adireekasw ktqiqydktn
181 vladfeqlrd ildweesnel qnlekeeedi lksltnsete mvqqtqslre lisdlehrlq
241 gsvmellqgv dgvikrtenv tlkkpetfpk nqrrvfrapd lkgmlevfre ltdvrrywvd
301 vtvapnnisc avisedkrqv sspkpqiiyx argtryqtfv nfnyctgilg sqsitsgkhy
361 wevdvskkta wilgvcagfq pdamcniekn enyqpkygyw vigleegvkc safqdssfht
421 psvpfivpls viicpdrvgv fldyeactvs ffnitnhgfl iykfshcsfs qpvfpylnpr
481 kcgvpmtlcs pss
``` wherein x is an acidic amino acid

FIG. 6E

Nucleotide sequence of rhesus macaque TRIM5α (SEQ ID NO: 27)

```
   1 gatgttggcc attacggccg gggtaggaaa attcctttgc gcagatcagg ccctggatt
  61 ggtgactgaa tcctaaccgt gtctttcctg gcctgccttc actcttctcc ccagactcac
 121 tacttctgca ctggtgtctg aaggtgtatt gagtgacttt gtggagggca gaagtaggaa
 181 gtctttggga caaaactgaa tttaccttgg gatctgtgaa caagacgaac ctcagcagcc
 241 aggacaggca ggagcagtgg agaagctgct atggcttctg gaatcctgct taatgtaaag
 301 gaggaggtga cctgtcccat ctgcctggaa ctcctgacag aaccctgag tctgcactgc
 361 ggccacagct tctgccaagc gtgcatcact gcgaaccaca agaagtccat gctatacaaa
 421 gaaggagaga gaagctgccc tgtgtgccgg atcagttacc agcctgagaa catacagcct
 481 aatcggcatg tagccaacat agtggagaag ctcagggagg tcaagttgag cccagaagag
 541 ggacagaagg ttgatcactg tgcacgccat ggagagaaac tcctactctt ctgtcaggag
 601 gacagcaagg tcatttgctg gctttgtgag cggtctcagg agcaccgtgg tcaccacact
 661 ttcctcatgg aggaggttgc ccaggagtac catgtgaagc tccagacagc tctggagatg
 721 ctgaggcaga agcagcagga agctgaaaag ttggaagctg acatcagaga agagaaagct
 781 tcctggaaga ttcaaataga ctacgacaaa accaacgtct cggcagattt tgagcaactg
 841 agagatcc tggactggga ggagagcaat gagctgcaga acctggagaa ggaggaagaa
 901 gacattctga aaagccttac gaagtctgaa acggagatgg tgcagcagac ccagtacatg
 961 agagagctca tctcagaact ggagcatcgg ttgcagggat caatgatgga tctactgcag
1021 ggtgtggatg gcatcattaa aaggattgag aacatgacct tgaagaagcc aaaaactttt
1081 cacaaaaatc aaaggagagt gtttcgagct cctgatctga aaggaatgct agacatgttt
1141 agagagctaa cagatgcccg acgctactgg gttgatgtga cactggctac aaacaacatt
1201 tcgcatgctg tcattgctga agataagaga caagtgagct ctcggaaccc acagataatg
1261 tatcaggcac cagggacatt atttacgttt ccgtcactca cgaattttcaa ttattgtact
1321 ggcgtcctgg gctcccaaag tatcacatca gggaagcatt actgggaggt agatgtgtcc
1381 aagaaagtg cttggatcct gggggtatgt gctggcttcc aatccgatgc aatgtataat
1441 attgaacaaa atgaaaatta tcaacctaaa tatggctact gggttatagg gttacaggaa
1501 ggagttaaat atagtgtttt ccaggatggt tcctcacata ctcctttgc tcctttcatt
1561 gtgccctct ctgtgattat ttgtcctgat cgtgttggag ttttcgtaga ctatgaggct
1621 tgcactgtct cattcttcaa tatcacaaac catggatttc tcatctataa gttttctcag
1681 tgttcttttt ctaagcctgt atttccatat ttaaatccca gaaatgtac agtcccatg
1741 actctgtgct caccaagctc ttgaacctt ttacacactc agccccttgt gtacagcacc
1801 tcttgtccat gtgcatctca tacacctgaa ctcagttgca tcatttaaac catctttcc
1861 ttgctgtctc tattcttct atttgaacgt cctgcactca tcagtgaaat gtgataatta
1921 tcttgtgcca tattctcccc aatattttat tgacatttga tagcaattgt tttcatcatt
1981 ttccatactc ccaaggaaaa ctgacctata cctcataaaa ggagaccact atttaggtat
2041 tacttctgcc aaatatttat catccagttg cctctgacac tgactaagaa gatgaaaaaa
2101 agctttctcaa cagccttct atatcatcgt gtgatagttg ttcaccaatg aatgagtcct
2161 tagtcctgtg tcagtttacc cttgatgccc ttatttgtga aagagttaaa gagaaaatat
2221 cataaatggt atactctaag tgtagaggtt ttgtatctag aggatctgag ttcaactcct
2281 gtctctccat gtactagcag tataactgtg aatagcatac ttaaatggct gtacttcttt
2341 tctttttctt ctttttttt ttttgagatg gagttttgct ctcattccc aggctggagt
2401 gaaatggtgc gatctcggct cactgcaacc tccgcttccc agattcaagc aattctccta
2461 cctcagcctc ccaagttgct gggattagag gggccacca ccaccccggg ctaaatttgt
2521 atttttacta gagacggggt ttccccatgt tgtgttggtt aggctcgtct aaaactcctg
2581 acctcaggtg atccaccccgc ctcggcctgc caaagtgctg ggattacagg catgagctac
2641 cgcgcccagc ctgtgcttat tttcttaaaa taattttgt attaaaaact tcccattaaa
2701 taagtcctaa atgtttttatc gcatagtagg gtgactagag ttaacaataa cattttgcat
2761 atatttgaa gtagctagaa gagaggattt tgaaagttct caacacgaag aaatgacaca
2821 tatttgaggt gatggatatg ctaattaccc tggtttgatt attacacaat atatacatat
2881 gtcaaaacat catactatac cacataaata tgtacattta ttatttgtca attaaaagca
2941 aaataaaaca aaaaccttc atctaatact tggatcatt gtgaaaaaat aaattcctga
3001 agtataaagc attaaaaaaa aaaaaaaaaa aaaaaaa
```

FIG. 7A

Amino acid sequence of rhesus macaque TRIM5α (SEQ ID NO: 28)

```
  1 masgillnvk eevtcpicle lteplslhc ghsfcqacit anhkksmlyk egerscpvcr
 61 isyqpeniqp nrhvanivek lrevklspee gqkvdhcarh geklllfcqe dskvicwlce
121 rsqehrghht flmeevaqey hvklqtalem lrqkqqeaek leadireeka swkiqidydk
181 tnvsadfeql reildweesn elqnlekeee dilksltkse temvqqtqym reliselehr
241 lqgsmmdllq gvdgiikrie nmtlkkpktf hknqrrvfra pdlkgmldmf reltdarryw
301 vdvtlatnni shaviaedkr qvssrnpqim yqapgtlftf psltnfnyct gvlgsqsits
361 gkhywevdvs kksawilgvc agfqsdamyn ieqnenyqpk ygywviglqe gvkysvfqdg
421 sshtpfapfi vplsviicpd rvgvfvdyca ctvsffnitn hgfliykfsq csfskpvfpy
481 lnprkctvpm tlcspss
```

FIG. 7B

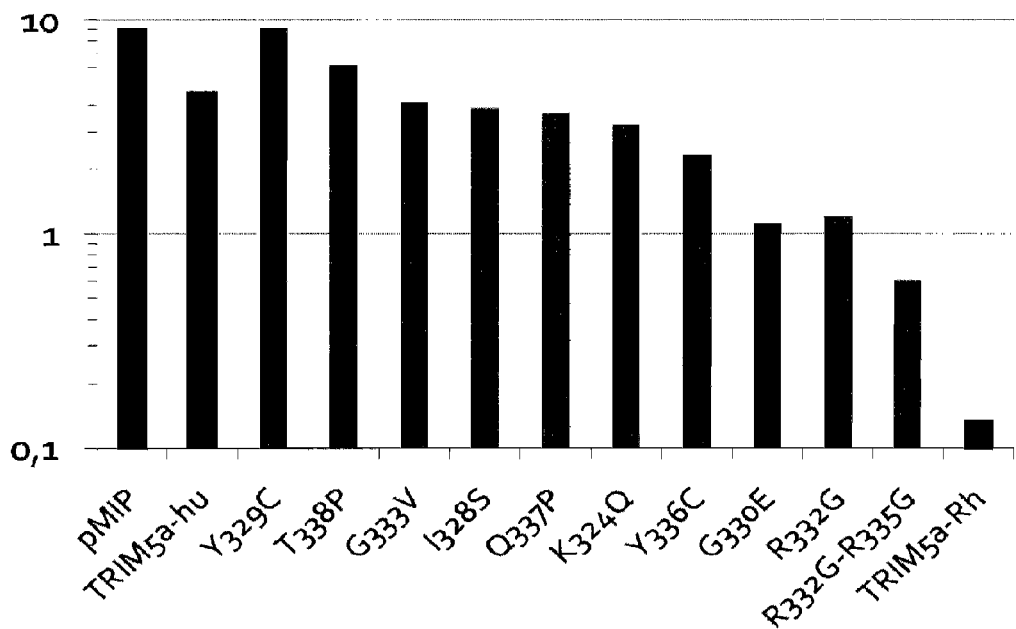

FIG. 8A

SEQUENCE LISTING

```
<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
acagatgtcc gacgctactg ggtt                                          24

<210> SEQ ID NO 2
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 2
tcctgaattc ttacttatcg tcgtcatcct tgtaatc                            37

<210> SEQ ID NO 3
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 3
gttcctcgag atggcttctg gaatcctggt taat                               34

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
aacccagtag cgtcggacat ctgt                                          24

<210> SEQ ID NO 5
<211> LENGTH: 25
<212> TYPE: DNA
<213> ORGANISM: Artificial Sequence
```

```
<220> FEATURE:
<223> OTHER INFORMATION: Synthetic oligonucleotide

<400> SEQUENCE: 5
atatggggca ggagggacaa gatac                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
cttgtccctc ctgccccata tatta                                              25

<210> SEQ ID NO 7
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 7
acgagggaca gactaccaga catttgt                                            27

<210> SEQ ID NO 8
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 8
atgtctggta gtctgtccct cgtgccc                                            27

<210> SEQ ID NO 9
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 9
acgagggaca gaataccaga catttg                                             26

<210> SEQ ID NO 10
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 10
tgtctggtat tctgtccctc gtgccc                                             26

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 11
acgagggaca ttctaccaga catttgt                                            27
```

```
<210> SEQ ID NO 12
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 12
atgtctggta gaatgtccct cgtgccc                                              27

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 13
acgagggaca ggataccaga cattt                                                25

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
gtctggtatc ctgtccctcg tgccc                                                25

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
cgagggacaa aataccagac atttg                                                25

<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 16
tgtctggtat tttgtccctc gtgcc                                                25

<210> SEQ ID NO 17
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 17
acgagggaca ttataccaga catttgt                                              27

<210> SEQ ID NO 18
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 18
```

```
atgtctggta taatgtccct cgtgccc                                         27
```

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 19

```
atatggggca ggagggacag aataccagac atttg                               35
```

<210> SEQ ID NO 20
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 20

```
tgtctggtat tctgtccctc ctgccccata tatta                               35
```

<210> SEQ ID NO 21
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 21

```
atatggggca ggagggacag gataccagac attt                                34
```

<210> SEQ ID NO 22
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 22

```
gtctggtatc ctgtccctcc tgccccatat atta                                34
```

<210> SEQ ID NO 23
<211> LENGTH: 3399
<212> TYPE: DNA
<213> ORGANISM: Homo sapiens
<220> FEATURE:
<221> NAME/KEY: CDS
<222> LOCATION: (304)..(1785)

<400> SEQUENCE: 23

```
agtttatctt tcactttcct gccctgagtg tgagcaagaa tttcctgcgg ttcctctagg    60
aaaattcctt tgtgcagatc aggcccgtgg attggtgagt gaatcctaac cacgtcttcc   120
ctggcctgtc ttcactcttc tccccagaat caccacttct gcactggtgt ctgaaggtgt   180
attgagtgat tttgtggagg gcagaagtag gaagtctttg gacaaaaact gtatttacct   240
tgggatctgt gaacaagagg aacctcagca gccaggacag gcaggagcag tggaatagct   300 act atg gct tct gga atc ctg gtt aat gta aag gag gag gtg acc tgc    348
    Met Ala Ser Gly Ile Leu Val Asn Val Lys Glu Glu Val Thr Cys
    1               5                  10                  15 ccc atc tgc ctg gaa ctc ctg aca caa ccc ctg agc ctg gac tgc ggc    396
Pro Ile Cys Leu Glu Leu Leu Thr Gln Pro Leu Ser Leu Asp Cys Gly
            20                  25                  30
```

```
cac agc ttc tgc caa gca tgc ctc act gca aac cac aag aag tcc atg      444
His Ser Phe Cys Gln Ala Cys Leu Thr Ala Asn His Lys Lys Ser Met
            35                  40                  45 cta gac aaa gga gag agt agc tgc cct gtg tgc cgg atc agt tac cag      492
Leu Asp Lys Gly Glu Ser Ser Cys Pro Val Cys Arg Ile Ser Tyr Gln
        50                  55                  60 cct gag aac ata cgg cct aat cgg cat gta gcc aac ata gtg gag aag      540
Pro Glu Asn Ile Arg Pro Asn Arg His Val Ala Asn Ile Val Glu Lys
    65                  70                  75 ctc agg gag gtc aag ttg agc cca gag ggg cag aaa gtt gat cat tgt      588
Leu Arg Glu Val Lys Leu Ser Pro Glu Gly Gln Lys Val Asp His Cys
80                  85                  90                  95 gca cgc cat gga gag aaa ctt cta ctc ttc tgt cag gag gac ggg aag      636
Ala Arg His Gly Glu Lys Leu Leu Leu Phe Cys Gln Glu Asp Gly Lys
                100                 105                 110 gtc att tgc tgg ctt tgt gag cgg tct cag gag cac cgt ggt cac cac      684
Val Ile Cys Trp Leu Cys Glu Arg Ser Gln Glu His Arg Gly His His
            115                 120                 125 acg ttc ctc aca gag gag gtt gcc cgg gag tac caa gtg aag ctc cag      732
Thr Phe Leu Thr Glu Glu Val Ala Arg Glu Tyr Gln Val Lys Leu Gln
        130                 135                 140 gca gct ctg gag atg ctg agg cag aag cag cag gaa gct gaa gag tta      780
Ala Ala Leu Glu Met Leu Arg Gln Lys Gln Gln Glu Ala Glu Glu Leu
145                 150                 155 gaa gct gac atc aga gaa gag aaa gct tcc tgg aag act caa ata cag      828
Glu Ala Asp Ile Arg Glu Glu Lys Ala Ser Trp Lys Thr Gln Ile Gln
160                 165                 170                 175 tat gac aaa acc aac gtc ttg gca gat ttt gag caa ctg aga gac atc      876
Tyr Asp Lys Thr Asn Val Leu Ala Asp Phe Glu Gln Leu Arg Asp Ile
                180                 185                 190 ctg gac tgg gag gag agc aat gag ctg caa aac ctg gag aag gag gag      924
Leu Asp Trp Glu Glu Ser Asn Glu Leu Gln Asn Leu Glu Lys Glu Glu
            195                 200                 205 gaa gac att ctg aaa agc ctt acg aac tct gaa act gag atg gtg cag      972
Glu Asp Ile Leu Lys Ser Leu Thr Asn Ser Glu Thr Glu Met Val Gln
        210                 215                 220 cag acc cag tcc ctg aga gag ctc atc tca gat ctg gag cat cgg ctg     1020
Gln Thr Gln Ser Leu Arg Glu Leu Ile Ser Asp Leu Glu His Arg Leu
225                 230                 235 cag ggg tca gtg atg gag ctg ctt cag ggt gtg gat ggc gtc ata aaa     1068
Gln Gly Ser Val Met Glu Leu Leu Gln Gly Val Asp Gly Val Ile Lys
240                 245                 250                 255 agg acg gag aac gtg acc ttg aag aag cca gaa act ttt cca aaa aat     1116
Arg Thr Glu Asn Val Thr Leu Lys Lys Pro Glu Thr Phe Pro Lys Asn
                260                 265                 270 caa agg aga gtg ttt cga gct cct gat ctg aaa gga atg cta gaa gtg     1164
Gln Arg Arg Val Phe Arg Ala Pro Asp Leu Lys Gly Met Leu Glu Val
            275                 280                 285 ttt aga gag ctg aca gat gtc cga cgc tac tgg gtt gat gtg aca gtg     1212
Phe Arg Glu Leu Thr Asp Val Arg Arg Tyr Trp Val Asp Val Thr Val
        290                 295                 300 gct cca aac aac att tca tgt gct gtc att tct gaa gat aag aga caa     1260
Ala Pro Asn Asn Ile Ser Cys Ala Val Ile Ser Glu Asp Lys Arg Gln
305                 310                 315 gtg agc tct ccg aaa cca cag ata ata tat ggg gca cga ggg aca aga     1308
Val Ser Ser Pro Lys Pro Gln Ile Ile Tyr Gly Ala Arg Gly Thr Arg
320                 325                 330                 335 tac cag aca ttt gtg aat ttc aat tat tgt act ggc atc ctg ggc tct     1356
Tyr Gln Thr Phe Val Asn Phe Asn Tyr Cys Thr Gly Ile Leu Gly Ser
                340                 345                 350
```

```
caa agt atc aca tca ggg aaa cat tac tgg gag gta gac gtg tcc aag    1404
Gln Ser Ile Thr Ser Gly Lys His Tyr Trp Glu Val Asp Val Ser Lys
            355                 360                 365 aaa act gct tgg atc ctg ggg gta tgt gct ggc ttc caa cct gat gca    1452
Lys Thr Ala Trp Ile Leu Gly Val Cys Ala Gly Phe Gln Pro Asp Ala
            370                 375                 380 atg tgt aat att gaa aaa aat gaa aat tat caa cct aaa tac ggc tac    1500
Met Cys Asn Ile Glu Lys Asn Glu Asn Tyr Gln Pro Lys Tyr Gly Tyr
        385                 390                 395 tgg gtt ata ggg tta gag gaa gga gtt aaa tgt agt gct ttc cag gat    1548
Trp Val Ile Gly Leu Glu Glu Gly Val Lys Cys Ser Ala Phe Gln Asp
400                 405                 410                 415 agt tcc ttc cat act cct tct gtt cct ttc att gtg ccc ctc tct gtg    1596
Ser Ser Phe His Thr Pro Ser Val Pro Phe Ile Val Pro Leu Ser Val
            420                 425                 430 att att tgt cct gat cgt gtt gga gtt ttc cta gac tat gag gct tgc    1644
Ile Ile Cys Pro Asp Arg Val Gly Val Phe Leu Asp Tyr Glu Ala Cys
            435                 440                 445 act gtc tca ttc ttc aat atc aca aac cat gga ttt ctc atc tat aag    1692
Thr Val Ser Phe Phe Asn Ile Thr Asn His Gly Phe Leu Ile Tyr Lys
            450                 455                 460 ttt tct cac tgt tct ttt tct cag cct gta ttt cca tat tta aat cct    1740
Phe Ser His Cys Ser Phe Ser Gln Pro Val Phe Pro Tyr Leu Asn Pro
        465                 470                 475 aga aaa tgt gga gtc ccc atg act ctg tgc tca cca agc tct tga        1785
Arg Lys Cys Gly Val Pro Met Thr Leu Cys Ser Pro Ser Ser
480                 485                 490 accttcttac acactcagcc ccttctgtac agcacctctt gtccaggtgc atctcataca   1845
cctgaactca tttgcatcat tttaaccatc ttttccttgc tgtctccctt ctttctattt   1905
gaacgtcctt cactcatcag taaaatgtaa taattgcctt gtgccatatt gtccccaata   1965
ttttattgac atttgatagc aattttttc atcattttcc gtactcctaa ggaaaactga    2025
cctatacctc ataaaatgag accgctattt aggtattact tctgccagat atttatcacc   2085
caattgcctc tgacactgac taagaagatg aagaaaagct tttcaacagc ctttctatat   2145
catcgtgtga taattgttca ccaatgaatg agtccttagc cctgtgtcag tttaccctcg   2205
atgcccttat tgtgagtta aagagaaaat atcataaatg gtatactctt aagtatagag    2265
gttttgtatc tagaggatct cagttcaact cctgtctctc catataccag cagtgtaact   2325
gtgaataaca tacttaaatg gctgtgctta tttccttttc ttttcttttt tctttttttt   2385 ttttttttgag atgaagtttt gctcttgttc cccaggctgg agtgcaatgg cacgatctcg   2445
gttcactgca acctccacct ctcagattca agcaattctc ctgcctcagc ctcccaagta   2505
gctgggatta caggtgccca ccaccacccc tggctaaatt tgtatttca gtagagacgg    2565 ggtttcccca tgttggttag gctcgtctag aacctctgac ctcaggtgat ccacccgcct   2625
cggcctccca agtgctggg attacaggcg tgagccacgg cgcccagcct gtgcttattt    2685
tcttaaaata attttgtat taaaaacttc acattaaata agtgctaatg ttttattgca    2745
tagtagggtg actagagtta acaataaccct attgcatata ttttgaaata gctagaagag   2805
aggattttga aagttctcaa cacaaagaaa tgacacatat ttgaggtgat ggatatgcta   2865
attaccctgg ttcggttatt acgcaatgta tacatgtatc aaaacatcac actgtaccac   2925
ataaatatgt atatttatta tttgtcaatt aaaagcaaaa taaacaaaa aaccttcatc    2985 taatactttg gatcattgtg aaaaaataaa ttcctgaagt ataaagcatc tatctaagtg   3045
tcttgatcta ataagtactt gttctacaaa ttattgaaaa acataaactc tgttaatgtc   3105
```

```
tcatggaaca ggttgtgcct tcagggaaac taggattgga tttactaaat tctcattttt   3165
tagatctcag atactactgt caaaatgact tcaattctgc cttctatata taatacacac   3225
atatatttag gattttattg taattctagt gttgctacat attagtcttt atcaaacaaa   3285
ctgaattatg tgggaatcag tttattaatt gtaaaaaata attataataa aattagctga   3345
tgtagttttt taaaagttaa acgagttttt tgaatagctt cactcatttc tagc         3399
```

<210> SEQ ID NO 24
<211> LENGTH: 493
<212> TYPE: PRT
<213> ORGANISM: Homo sapiens

<400> SEQUENCE: 24

```
Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
                20                  25                  30

Ser Phe Cys Gln Ala Cys Leu Thr Ala Asn His Lys Lys Ser Met Leu
            35                  40                  45

Asp Lys Gly Glu Ser Ser Cys Pro Val Cys Arg Ile Ser Tyr Gln Pro
        50                  55                  60

Glu Asn Ile Arg Pro Asn Arg His Val Ala Asn Ile Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Leu Thr Glu Glu Val Ala Arg Glu Tyr Gln Val Lys Leu Gln Ala
130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
    290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Arg Gly Thr Arg Tyr
                325                 330                 335
```

```
Gln Thr Phe Val Asn Phe Asn Tyr Cys Thr Gly Ile Leu Gly Ser Gln
            340                 345                 350

Ser Ile Thr Ser Gly Lys His Tyr Trp Glu Val Asp Val Ser Lys Lys
            355                 360                 365

Thr Ala Trp Ile Leu Gly Val Cys Ala Gly Phe Gln Pro Asp Ala Met
370                 375                 380

Cys Asn Ile Glu Lys Asn Glu Asn Tyr Gln Pro Lys Tyr Gly Tyr Trp
385                 390                 395                 400

Val Ile Gly Leu Glu Glu Gly Val Lys Cys Ser Ala Phe Gln Asp Ser
            405                 410                 415

Ser Phe His Thr Pro Ser Val Pro Phe Ile Val Pro Leu Ser Val Ile
            420                 425                 430

Ile Cys Pro Asp Arg Val Gly Val Phe Leu Asp Tyr Glu Ala Cys Thr
            435                 440                 445

Val Ser Phe Phe Asn Ile Thr Asn His Gly Phe Leu Ile Tyr Lys Phe
450                 455                 460

Ser His Cys Ser Phe Ser Gln Pro Val Phe Pro Tyr Leu Asn Pro Arg
465                 470                 475                 480

Lys Cys Gly Val Pro Met Thr Leu Cys Ser Pro Ser Ser
                485                 490
```

<210> SEQ ID NO 25
<211> LENGTH: 493
<212> TYPE: PRT
<213> ORGANISM: Homo sapiens
<220> FEATURE:
<221> NAME/KEY: MISC_FEATURE
<222> LOCATION: (335)..(335)
<223> OTHER INFORMATION: Xaa at position 335 is Asp, Glu, Gly, Lys or is absent

<400> SEQUENCE: 25

```
Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
50                  55                  60

Glu Asn Ile Arg Pro Asn Arg His Val Ala Asn Leu Val Glu Lys Leu
65                  70                  75                  80

Arg Glu Val Lys Leu Ser Pro Glu Gly Gln Lys Val Asp His Cys Ala
            85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
            165                 170                 175

Asp Lys Thr Asn Val Leu Ala Asp Phe Glu Gln Leu Arg Asp Ile Leu
            180                 185                 190
```

```
Asp Trp Glu Glu Ser Asn Glu Leu Gln Asn Leu Glu Lys Glu Glu
            195                 200                 205

Asp Ile Leu Lys Ser Leu Thr Asn Ser Glu Thr Glu Met Val Gln Gln
210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
    290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Arg Gly Thr Xaa Tyr
                325                 330                 335

Gln Thr Phe Val Asn Phe Asn Tyr Cys Thr Gly Ile Leu Gly Ser Gln
            340                 345                 350

Ser Ile Thr Ser Gly Lys His Tyr Trp Glu Val Asp Val Ser Lys Lys
        355                 360                 365

Thr Ala Trp Ile Leu Gly Val Cys Ala Gly Phe Gln Pro Asp Ala Met
    370                 375                 380

Cys Asn Ile Glu Lys Asn Glu Asn Tyr Gln Pro Lys Tyr Gly Tyr Trp
385                 390                 395                 400

Val Ile Gly Leu Glu Glu Gly Val Lys Cys Ser Ala Phe Gln Asp Ser
                405                 410                 415

Ser Phe His Thr Pro Ser Val Pro Phe Ile Val Pro Leu Ser Val Ile
            420                 425                 430

Ile Cys Pro Asp Arg Val Gly Val Phe Leu Asp Tyr Glu Ala Cys Thr
        435                 440                 445

Val Ser Phe Phe Asn Ile Thr Asn His Gly Phe Leu Ile Tyr Lys Phe
    450                 455                 460

Ser His Cys Ser Phe Ser Gln Pro Val Phe Pro Tyr Leu Asn Pro Arg
465                 470                 475                 480

Lys Cys Gly Val Pro Met Thr Leu Cys Ser Pro Ser Ser
                485                 490

<210> SEQ ID NO 26
<211> LENGTH: 493
<212> TYPE: PRT
<213> ORGANISM: Homo sapiens
<220> FEATURE:
<221> NAME/KEY: MISC_FEATURE
<222> LOCATION: (335)..(335)
<223> OTHER INFORMATION: Xaa at position 335 is Asp, Glu, Gly, Lys or is
      absent

<400> SEQUENCE: 26

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
                20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
```

-continued

```
            50                  55                  60
Glu Asn Ile Arg Pro Asn Arg His Val Ala Asn Leu Val Glu Lys Leu
 65                  70                  75                  80

Arg Glu Val Lys Leu Ser Pro Glu Gly Gln Lys Val Asp His Cys Ala
                 85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Gly Gly Thr Xaa Tyr
                325                 330                 335

Gln Thr Phe Val Asn Phe Asn Tyr Cys Thr Gly Ile Leu Gly Ser Gln
            340                 345                 350

Ser Ile Thr Ser Gly Lys His Tyr Trp Glu Val Asp Val Ser Lys Lys
        355                 360                 365

Thr Ala Trp Ile Leu Gly Val Cys Ala Gly Phe Gln Pro Asp Ala Met
370                 375                 380

Cys Asn Ile Glu Lys Asn Glu Asn Tyr Gln Pro Lys Tyr Gly Tyr Trp
385                 390                 395                 400

Val Ile Gly Leu Glu Glu Gly Val Lys Cys Ser Ala Phe Gln Asp Ser
                405                 410                 415

Ser Phe His Thr Pro Ser Val Pro Phe Ile Val Pro Leu Ser Val Ile
            420                 425                 430

Ile Cys Pro Asp Arg Val Gly Val Phe Leu Asp Tyr Glu Ala Cys Thr
        435                 440                 445

Val Ser Phe Phe Asn Ile Thr Asn His Gly Phe Leu Ile Tyr Lys Phe
450                 455                 460

Ser His Cys Ser Phe Ser Gln Pro Val Phe Pro Tyr Leu Asn Pro Arg
465                 470                 475                 480
```

```
              Lys Cys Gly Val Pro Met Thr Leu Cys Ser Pro Ser Ser
                              485                 490

<210> SEQ ID NO 27
<211> LENGTH: 1494
<212> TYPE: DNA
<213> ORGANISM: Macaca mulatta
<220> FEATURE:
<221> NAME/KEY: CDS
<222> LOCATION: (1)..(1494)

<400> SEQUENCE: 27 atg gct tct gga atc ctg ctt aat gta aag gag gag gtg acc tgt ccc         48
Met Ala Ser Gly Ile Leu Leu Asn Val Lys Glu Glu Val Thr Cys Pro
1               5                   10                  15 atc tgc ctg gaa ctc ctg aca gaa ccc ctg agt ctg cac tgc ggc cac         96
Ile Cys Leu Glu Leu Leu Thr Glu Pro Leu Ser Leu His Cys Gly His
            20                  25                  30 agc ttc tgc caa gcg tgc atc act gcg aac cac aag aag tcc atg cta        144
Ser Phe Cys Gln Ala Cys Ile Thr Ala Asn His Lys Lys Ser Met Leu
        35                  40                  45 tac aaa gaa gga gag aga agc tgc cct gtg tgc cgg atc agt tac cag        192
Tyr Lys Glu Gly Glu Arg Ser Cys Pro Val Cys Arg Ile Ser Tyr Gln
    50                  55                  60 cct gag aac ata cag cct aat cgg cat gta gcc aac ata gtg gag aag        240
Pro Glu Asn Ile Gln Pro Asn Arg His Val Ala Asn Ile Val Glu Lys
65                  70                  75                  80 ctc agg gag gtc aag ttg agc cca gaa gag ggg cag aag gtt gat cac        288
Leu Arg Glu Val Lys Leu Ser Pro Glu Glu Gly Gln Lys Val Asp His
                85                  90                  95 tgt gca cgc cat gga gag aaa ctc cta ctc ttc tgt cag gag gac agc        336
Cys Ala Arg His Gly Glu Lys Leu Leu Leu Phe Cys Gln Glu Asp Ser
            100                 105                 110 aag gtc att tgc tgg ctt tgt gag cgg tct cag gag cac cgt ggt cac        384
Lys Val Ile Cys Trp Leu Cys Glu Arg Ser Gln Glu His Arg Gly His
        115                 120                 125 cac act ttc ctc atg gag gag gtt gcc cag gag tac cat gtg aag ctc        432
His Thr Phe Leu Met Glu Glu Val Ala Gln Glu Tyr His Val Lys Leu
    130                 135                 140 cag aca gct ctg gag atg ctg agg cag aag cag cag gaa gct gaa aag        480
Gln Thr Ala Leu Glu Met Leu Arg Gln Lys Gln Gln Glu Ala Glu Lys
145                 150                 155                 160 ttg gaa gct gac atc aga gaa gag aaa gct tcc tgg aag att caa ata        528
Leu Glu Ala Asp Ile Arg Glu Glu Lys Ala Ser Trp Lys Ile Gln Ile
                165                 170                 175 gac tac gac aaa acc aac gtc tcg gca gat ttt gag caa ctg aga gag        576
Asp Tyr Asp Lys Thr Asn Val Ser Ala Asp Phe Glu Gln Leu Arg Glu
            180                 185                 190 atc ctg gac tgg gag gag agc aat gag ctg cag aac ctg gag aag gag        624
Ile Leu Asp Trp Glu Glu Ser Asn Glu Leu Gln Asn Leu Glu Lys Glu
        195                 200                 205 gaa gaa gac att ctg aaa agc ctt acg aag tct gaa atg gag atg gtg        672
Glu Glu Asp Ile Leu Lys Ser Leu Thr Lys Ser Glu Met Glu Met Val
    210                 215                 220 cag cag acc cag tac atg aga gag ctc atc tca gaa ctg gag cat cgg        720
Gln Gln Thr Gln Tyr Met Arg Glu Leu Ile Ser Glu Leu Glu His Arg
225                 230                 235                 240 ttg cag ggg tca atg atg gat cta ctg cag ggt gtg gat ggc atc att        768
Leu Gln Gly Ser Met Met Asp Leu Leu Gln Gly Val Asp Gly Ile Ile
                245                 250                 255 aaa agg att gag aac atg acc ttg aag aag cca aaa act ttt cac aaa        816
Lys Arg Ile Glu Asn Met Thr Leu Lys Lys Pro Lys Thr Phe His Lys
```

```
                        260                 265                 270
aat caa agg aga gtg ttt cga gct cct gat ctg aaa gga atg cta gac        864
Asn Gln Arg Arg Val Phe Arg Ala Pro Asp Leu Lys Gly Met Leu Asp
        275                 280                 285 atg ttt aga gag cta aca gat gcc cga cgc tac tgg gtt gat gtg aca        912
Met Phe Arg Glu Leu Thr Asp Ala Arg Arg Tyr Trp Val Asp Val Thr
        290                 295                 300 ctg gct cca aac aac att tcg cat gct gtc att gct gaa gat aag aga        960
Leu Ala Pro Asn Asn Ile Ser His Ala Val Ile Ala Glu Asp Lys Arg
305                 310                 315                 320 caa gtg agc tct cgg aac cca cag ata atg tat cag gca cca ggg aca       1008
Gln Val Ser Ser Arg Asn Pro Gln Ile Met Tyr Gln Ala Pro Gly Thr
                325                 330                 335 tta ttt acg ttt ccg tca ctc acg aat ttc aat tat tgt act ggc gtc       1056
Leu Phe Thr Phe Pro Ser Leu Thr Asn Phe Asn Tyr Cys Thr Gly Val
                340                 345                 350 ctg ggc tcc caa agt atc aca tca ggg aag cat tac tgg gag gta gat       1104
Leu Gly Ser Gln Ser Ile Thr Ser Gly Lys His Tyr Trp Glu Val Asp
                355                 360                 365 gtg tcc aag aaa agt gct tgg atc ctg ggg gta tgt gct ggc ttc caa       1152
Val Ser Lys Lys Ser Ala Trp Ile Leu Gly Val Cys Ala Gly Phe Gln
        370                 375                 380 tcc gat gca atg tat aat att gaa caa aat gaa aat tat caa cct aaa       1200
Ser Asp Ala Met Tyr Asn Ile Glu Gln Asn Glu Asn Tyr Gln Pro Lys
385                 390                 395                 400 tat ggc tac tgg gtt ata ggg tta cag gaa gga gtt aaa tat agt gtt       1248
Tyr Gly Tyr Trp Val Ile Gly Leu Gln Glu Gly Val Lys Tyr Ser Val
                405                 410                 415 ttc cag gat ggt tcc tca cat act cct ttt gct cct ttc att gtg ccc       1296
Phe Gln Asp Gly Ser Ser His Thr Pro Phe Ala Pro Phe Ile Val Pro
                420                 425                 430 ctc tct gtg att att tgt cct gat cgt gtt gga gtt ttc gta gac tat       1344
Leu Ser Val Ile Ile Cys Pro Asp Arg Val Gly Val Phe Val Asp Tyr
                435                 440                 445 gag gct tgc act gtc tca ttc ttc aat atc aca aac cat gga ttt ctc       1392
Glu Ala Cys Thr Val Ser Phe Phe Asn Ile Thr Asn His Gly Phe Leu
        450                 455                 460 atc tat aag ttt tct cag tgt tct ttt tct aag cct gta ttt cca tat       1440
Ile Tyr Lys Phe Ser Gln Cys Ser Phe Ser Lys Pro Val Phe Pro Tyr
465                 470                 475                 480 tta aat ccc aga aaa tgt aca gtc ccc atg act ctg tgc tca cca agc       1488
Leu Asn Pro Arg Lys Cys Thr Val Pro Met Thr Leu Cys Ser Pro Ser
                485                 490                 495 tct tga                                                                1494
Ser

<210> SEQ ID NO 28
<211> LENGTH: 497
<212> TYPE: PRT
<213> ORGANISM: Macaca mulatta

<400> SEQUENCE: 28

Met Ala Ser Gly Ile Leu Leu Asn Val Lys Glu Glu Val Thr Cys Pro
1               5                   10                  15

Ile Cys Leu Glu Leu Leu Thr Glu Pro Leu Ser Leu His Cys Gly His
                20                  25                  30

Ser Phe Cys Gln Ala Cys Ile Thr Ala Asn His Lys Lys Ser Met Leu
            35                  40                  45

Tyr Lys Glu Gly Glu Arg Ser Cys Pro Val Cys Arg Ile Ser Tyr Gln
        50                  55                  60
```

```
Pro Glu Asn Ile Gln Pro Asn Arg His Val Ala Asn Ile Val Glu Lys
 65                  70                  75                  80

Leu Arg Glu Val Lys Leu Ser Pro Glu Glu Gly Gln Lys Val Asp His
                 85                  90                  95

Cys Ala Arg His Gly Glu Lys Leu Leu Leu Phe Cys Gln Glu Asp Ser
                100                 105                 110

Lys Val Ile Cys Trp Leu Cys Glu Arg Ser Gln Glu His Arg Gly His
            115                 120                 125

His Thr Phe Leu Met Glu Glu Val Ala Gln Glu Tyr His Val Lys Leu
        130                 135                 140

Gln Thr Ala Leu Glu Met Leu Arg Gln Lys Gln Glu Ala Glu Lys
145                 150                 155                 160

Leu Glu Ala Asp Ile Arg Glu Glu Lys Ala Ser Trp Lys Ile Gln Ile
                165                 170                 175

Asp Tyr Asp Lys Thr Asn Val Ser Ala Asp Phe Glu Gln Leu Arg Glu
            180                 185                 190

Ile Leu Asp Trp Glu Glu Ser Asn Glu Leu Gln Asn Leu Glu Lys Glu
        195                 200                 205

Glu Glu Asp Ile Leu Lys Ser Leu Thr Lys Ser Glu Met Glu Met Val
    210                 215                 220

Gln Gln Thr Gln Tyr Met Arg Glu Leu Ile Ser Glu Leu Glu His Arg
225                 230                 235                 240

Leu Gln Gly Ser Met Met Asp Leu Leu Gln Gly Val Asp Gly Ile Ile
                245                 250                 255

Lys Arg Ile Glu Asn Met Thr Leu Lys Lys Pro Lys Thr Phe His Lys
            260                 265                 270

Asn Gln Arg Arg Val Phe Arg Ala Pro Asp Leu Lys Gly Met Leu Asp
        275                 280                 285

Met Phe Arg Glu Leu Thr Asp Ala Arg Arg Tyr Trp Val Asp Val Thr
    290                 295                 300

Leu Ala Pro Asn Asn Ile Ser His Ala Val Ile Ala Glu Asp Lys Arg
305                 310                 315                 320

Gln Val Ser Ser Arg Asn Pro Gln Ile Met Tyr Gln Ala Pro Gly Thr
                325                 330                 335

Leu Phe Thr Phe Pro Ser Leu Thr Asn Phe Asn Tyr Cys Thr Gly Val
            340                 345                 350

Leu Gly Ser Gln Ser Ile Thr Ser Gly Lys His Tyr Trp Glu Val Asp
        355                 360                 365

Val Ser Lys Lys Ser Ala Trp Ile Leu Gly Val Cys Ala Gly Phe Gln
    370                 375                 380

Ser Asp Ala Met Tyr Asn Ile Glu Gln Asn Glu Asn Tyr Gln Pro Lys
385                 390                 395                 400

Tyr Gly Tyr Trp Val Ile Gly Leu Gln Glu Gly Val Lys Tyr Ser Val
                405                 410                 415

Phe Gln Asp Gly Ser Ser His Thr Pro Phe Ala Pro Phe Ile Val Pro
            420                 425                 430

Leu Ser Val Ile Ile Cys Pro Asp Arg Val Gly Val Phe Val Asp Tyr
        435                 440                 445

Glu Ala Cys Thr Val Ser Phe Phe Asn Ile Thr Asn His Gly Phe Leu
    450                 455                 460

Ile Tyr Lys Phe Ser Gln Cys Ser Phe Ser Lys Pro Val Phe Pro Tyr
465                 470                 475                 480

Leu Asn Pro Arg Lys Cys Thr Val Pro Met Thr Leu Cys Ser Pro Ser
```

Ser

<210> SEQ ID NO 29
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 29

```
agacaagtga gctctccgaa accacagata atatatgggg cacgagggac aagataccag    60
acatttgtga atttcaatta ttgtact                                        87
```

<210> SEQ ID NO 30
<211> LENGTH: 493
<212> TYPE: PRT
<213> ORGANISM: Homo sapiens
<220> FEATURE:
<221> NAME/KEY: MISC_FEATURE
<222> LOCATION: (330)..(330)
<223> OTHER INFORMATION: Xaa at position 330 is an acidic amino acid

<400> SEQUENCE: 30

```
Met Ala Ser Gly Ile Leu Val Asn Val Lys Glu Glu Val Thr Cys Pro
  1               5                  10                  15

Ile Cys Leu Glu Leu Leu Thr Gln Pro Leu Ser Leu Asp Cys Gly His
                 20                  25                  30

Ser Phe Cys Gln Ala Cys Leu Thr Ala Asn His Lys Lys Ser Met Leu
             35                  40                  45

Asp Lys Gly Glu Ser Ser Cys Pro Val Cys Arg Ile Ser Tyr Gln Pro
         50                  55                  60

Glu Asn Ile Arg Pro Asn Arg His Val Ala Asn Leu Val Glu Lys Leu
 65                  70                  75                  80

Arg Glu Val Lys Leu Ser Pro Glu Gly Gln Lys Val Asp His Cys Ala
                 85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270
```

```
Arg Arg Val Phe Arg Ala Pro Asp Leu Lys Gly Met Leu Glu Val Phe
        275                 280                 285
Arg Glu Leu Thr Asp Val Arg Arg Tyr Trp Val Asp Val Thr Val Ala
        290                 295                 300
Pro Asn Asn Ile Ser Cys Ala Val Ile Ser Glu Asp Lys Arg Gln Val
305                 310                 315                 320
Ser Ser Pro Lys Pro Gln Ile Ile Tyr Xaa Ala Arg Gly Thr Arg Tyr
                325                 330                 335
Gln Thr Phe Val Asn Phe Asn Tyr Cys Thr Gly Ile Leu Gly Ser Gln
            340                 345                 350
Ser Ile Thr Ser Gly Lys His Tyr Trp Glu Val Asp Val Ser Lys Lys
            355                 360                 365
Thr Ala Trp Ile Leu Gly Val Cys Ala Gly Phe Gln Pro Asp Ala Met
        370                 375                 380
Cys Asn Ile Glu Lys Asn Glu Asn Tyr Gln Pro Lys Tyr Gly Tyr Trp
385                 390                 395                 400
Val Ile Gly Leu Glu Glu Gly Val Lys Cys Ser Ala Phe Gln Asp Ser
                405                 410                 415
Ser Phe His Thr Pro Ser Val Pro Phe Ile Val Pro Leu Ser Val Ile
            420                 425                 430
Ile Cys Pro Asp Arg Val Gly Val Phe Leu Asp Tyr Glu Ala Cys Thr
        435                 440                 445
Val Ser Phe Phe Asn Ile Thr Asn His Gly Phe Leu Ile Tyr Lys Phe
        450                 455                 460
Ser His Cys Ser Phe Ser Gln Pro Val Phe Pro Tyr Leu Asn Pro Arg
465                 470                 475                 480
Lys Cys Gly Val Pro Met Thr Leu Cys Ser Pro Ser Ser
                485                 490
```

TRIM5ALPHA MUTANTS AND USES THEREOF

CROSS REFERENCE TO RELATED APPLICATIONS

This application is a National Entry Application of PCT application no PCT/CA2010/001882 filed on Nov. 19, 2010 and published in English under PCT Article 21(2), which itself claims the benefit of U.S. Provisional Patent Application Ser. No. 61/263,594 filed on Nov. 23, 2009. All documents noted above are incorporated herein by reference in their entirety.

SEQUENCE LISTING

Pursuant to 37 C.F.R. 1.821(c), a sequence listing is submitted herewith as an ASCII compliant text file named "15690_2_SeqListing_ST25.txt", created on May 23, 2012 and having a size of 43 kilobytes. The content of the aforementioned file is hereby incorporated by reference in its entirety.

TECHNICAL FIELD

The present invention generally relates to the treatment of viral infection and associated conditions, and more particularly to the treatment of retroviral infection and associated conditions, such as HIV infection and AIDS.

BACKGROUND ART

Retroviruses are small enveloped viruses that contain a diploid, single-stranded RNA genome, and replicate via a DNA intermediate produced by a virally-encoded reverse transcriptase, an RNA-dependent DNA polymerase. Retroviruses include, for example, oncogenic viruses such as human T-cell leukemia viruses (HTLV-I, -II, -III), and feline leukemia virus as well as Human Immunodeficiency Virus (HIV-1 and HIV-2). HIV-1 is a member of the lentivirus family of retroviruses which contains a single-stranded RNA genome and is considered the major etiological agent involved in the development of acquired immunodeficiency syndrome (AIDS) and related disorders. The World Health Organization (WHO) estimates that as of the end of 2007 over 42 million people worldwide are infected and this number is growing. A great deal of effort to develop drugs against HIV has been centered around HIV reverse transcriptase (RT), HIV protease, and more recently viral entry.

Numerous gene therapy clinical trials for the treatment of AIDS have been undertaken yielding mostly disappointing results, both in terms of viral load and of CD4$^+$ T cells counts (Rossi, J. J., et al., 2007. *Nat Biotechnol* 25:1444-54). In particular, while it is desirable that transgene-expressing cells survive and proliferate in the recipient patients, the opposite is often seen. For instance, following gene transfer of an anti-HIV ribozyme in hematopoietic stem cells, a 5-fold reduction in expression of the ribozyme was observed within 6 months (Mitsuyasu, R. T. et al., 2009. *Nat Med* 15:285-92). Rapid elimination of productively HIV-1-infected lymphocytes is well-known (Coffin, J. M., 1995. *Science* 267:483-9.) and results from the action of cytotoxic T lymphocytes (CTLs) and also from virus-related apoptosis.

None of the current AIDS treatments have proven to be totally effective in treating and/or reversing the disease. In addition, many of the compounds currently used to treat AIDS cause adverse side effects including low platelet count, renal toxicity and bone marrow cytopenia.

Thus, there continues to be a significant need for new therapeutic strategies for retroviral infections such as HIV infection and associated conditions such as AIDS.

The present description refers to a number of documents, the content of which is herein incorporated by reference in their entirety.

SUMMARY OF THE INVENTION

The present invention provides the following 1 to 56:

1. A mutant tripartite motif-containing 5 alpha (TRIM5α) polypeptide conferring a higher resistance to a lentivirus infection relative to wild-type human TRIM5α, said mutant TRIM5α polypeptide comprising a first mutation at an amino acid corresponding to amino acid 324, 328, 330, 333, 335, 336 or 337 of wild-type human TRIM5α, wherein said mutation at an amino acid corresponding to amino acid 335 is a deletion, a substitution with a Glu residue, a substitution with an Asp residue, a substitution with a Lys residue, or a substitution with a Gly residue.

2. The mutant TRIM5α polypeptide of 1, wherein said first mutation is at an amino acid corresponding to amino acid 335 of wild-type human TRIM5α.

3. The mutant TRIM5α polypeptide of 2, comprising residues 321 to 346 of the amino acid sequence of SEQ ID NO: 25.

4. The mutant TRIM5α polypeptide of 2, further comprising a second mutation at an amino acid corresponding to amino acid 332 of wild-type human TRIM5α.

5. The mutant TRIM5α polypeptide of 4, wherein said second mutation is a substitution with a Gly residue.

6. The mutant TRIM5α polypeptide of 5, comprising residues 321 to 346 of the amino acid sequence of SEQ ID NO: 26.

7. The mutant TRIM5α polypeptide of any one of 1 to 6, comprising residues 281 to 320 and 347 to 493 of the amino acid sequence of SEQ ID NO: 25.

8. The mutant TRIM5α polypeptide of any one of 1 to 7, further comprising residues 15 to 59 of the amino acid sequence of SEQ ID NO: 25.

9. The mutant TRIM5α polypeptide of any one of 1 to 8, further comprising residues 90 to 132 of the amino acid sequence of SEQ ID NO: 25.

10. The mutant TRIM5α polypeptide of any one of 1 to 9, further comprising residues 130 to 241 of the amino acid sequence of SEQ ID NO: 25.

11. The mutant TRIM5α polypeptide of 3, comprising the amino acid sequence of SEQ ID NO: 25.

12. The mutant TRIM5α polypeptide of 5, comprising the amino acid sequence of SEQ ID NO: 26.

13. The mutant TRIM5α polypeptide of 1, wherein said first mutation is a substitution with any acidic amino acid residue other than the wild-type residue at position 324, 328, 330, 333, 336 or 337 of wild-type human TRIM5α.

14. The mutant TRIM5α polypeptide of 13, wherein said first mutation is at an amino acid corresponding to amino acid 330 of wild-type human TRIM5α

15. The mutant TRIM5α polypeptide of 14, comprising residues 321 to 346 of the amino acid sequence of SEQ ID NO: 30.

16. The mutant TRIM5α polypeptide of 14 or 15, comprising residues 281 to 320 and 347 to 493 of the amino acid sequence of SEQ ID NO: 30.

17. The mutant TRIM5α polypeptide of any one of 14 to 16, further comprising residues 15 to 59 of the amino acid sequence of SEQ ID NO: 30.

18. The mutant TRIM5α polypeptide of any one of 14 to 17, further comprising residues 90 to 132 of the amino acid sequence of SEQ ID NO: 30.

19. The mutant TRIM5α polypeptide of any one of 14 to 18, further comprising residues 130 to 241 of the amino acid sequence of SEQ ID NO: 30.

20. The mutant TRIM5α polypeptide of 14, comprising the amino acid sequence of SEQ ID NO: 30.

21. The mutant TRIM5α polypeptide of any one of 13 to 20, wherein said mutation at position 330 is a substitution with a Glu residue.

22. The mutant TRIM5α polypeptide of 13, wherein said mutation at position 324 is a substitution with a Gln residue, said mutation at position 328 is a substitution with a Ser residue, said mutation at position 333 is a substitution with a Val residue, said mutation at position 336 is a substitution with a Cys residue, and said mutation at position 337 is a substitution with a Pro residue.

23. The mutant TRIM5α polypeptide of any one of 1 to 22, wherein said mutant TRIM5α polypeptide comprises: (i) a Gly to Glu substitution at an amino acid corresponding to amino acid 330 of wild-type human TRIM5α; (ii) an Arg to Gly substitution at an amino acid corresponding to amino acid 332 of wild-type human TRIM5α; and (iii) an Arg to Gly substitution at an amino acid corresponding to amino acid 335 of wild-type human TRIM5α.

24. The mutant TRIM5α polypeptide of any one of 1 to 23, wherein said lentivirus infection is human immunodeficiency infection (HIV).

25. A nucleic acid encoding the mutant TRIM5α polypeptide of any one of 1 to 24.

26. The nucleic acid of 25, comprising an adenine to guanine substitution at a nucleotide corresponding to nucleotide 1003 of wild-type human TRIM5α.

27. The nucleic acid of 25, comprising a guanine to adenine substitution at a nucleotide corresponding to nucleotide 989 of wild-type human TRIM5α.

28. A vector comprising the nucleic acid of any one of 25 to 27.

29. The vector of 28, wherein said vector is a gene therapy vector.

30. A cell comprising (i) the mutant TRIM5α polypeptide of any one of 1 to 24; (ii) the nucleic acid of any one of 25 to 27; and/or (iii) the vector of 28 or 29.

31. The cell of 30, wherein said cell is a mammalian cell.

32. The cell of 31, wherein said mammalian cell is a hematopoietic stem cell (HSC).

33. A composition comprising (i) the mutant TRIM5α polypeptide of any one of 1 to 23; (ii) the nucleic acid of any one of 25 to 27; (iii) the vector of 28 or 29; and/or (iv) the cell of any one of 30 to 32, and a pharmaceutically acceptable carrier.

34. An antibody specifically recognizing the mutant TRIM5α polypeptide of any one of 1 to 24.

35. A method for preventing or treating a lentivirus infection in a subject in need thereof, said method comprising administering to said subject in need thereof an effective amount of (i) the mutant TRIM5α polypeptide of any one of 1 to 24; (ii) the nucleic acid of any one of 25 to 27; (iii) the vector of 28 or 29; (iv) the cell of any one of 30 to 32 and/or (v) the composition of 33.

36. The method of 34, wherein said method comprises; (a) introducing the nucleic acid of any one of 25 to 27 and/or the vector of 28 or 29 into a donor cell; and (b) administering an effective amount of the donor cell to said subject.

37. The method of 36, wherein said donor cell is obtained from said subject.

38. The method of any one of 35 to 37, wherein said lentivirus infection is human immunodeficiency infection (HIV).

39. Use of (i) the mutant TRIM5α polypeptide of any one of 1 to 24; (ii) the nucleic acid of any one of 25 to 27; (iii) the vector of 28 or 29; (iv) the cell of any one of 30 to 32 and/or (v) the composition of 33, as a medicament.

40. Use of (i) the mutant TRIM5α polypeptide of any one of 1 to 24; (ii) the nucleic acid of any one of 25 to 27; (iii) the vector of 28 or 29; (iv) the cell of any one of 30 to 32 and/or (v) the composition of 33, for preventing or treating a lentivirus infection in a subject.

41. Use of (i) the mutant TRIM5α polypeptide of any one of 1 to 24; (ii) the nucleic acid of any one of 25 to 27; (iii) the vector of 28 or 29; (iv) the cell of any one of 30 to 32 and/or (v) the composition of 33, for the preparation of a medicament for preventing or treating a lentivirus infection in a subject.

42. The use of 40 or 41, wherein said lentivirus infection is human immunodeficiency virus (HIV) infection.

43. An agent selected from: (i) the mutant TRIM5α polypeptide of any one of 1 to 24; (ii) the nucleic acid of any one of 25 to 27; (iii) the vector of 28 or 29; (iv) the cell of any one of 30 to 32 and/or (v) the composition of 33, for preventing or treating a lentivirus infection in a subject.

44. The agent of 43, wherein said lentivirus infection is human immunodeficiency virus (HIV) infection.

45. A method for determining whether a subject has an increased resistance to lentivirus infection, said method comprising determining, in a biological sample from said subject, the presence or absence of (i) the mutant TRIM5α polypeptide of any one of 1 to 24; (ii) the nucleic acid of any one of 25 to 27; wherein the presence of said mutant TRIM5αpolypeptide and/or nucleic acid is indicative that said subject has an increased resistance to lentivirus infection.

46. The method of 45, wherein said lentivirus infection is human immunodeficiency virus (HIV) infection.

47. A kit for determining whether a subject has an increased resistance to lentivirus infection, said kit comprising (a) means for detecting the presence or absence of (i) the mutant TRIM5α polypeptide of any one of 1 to 24; (ii) the nucleic acid of any one of 25 to 27.

48. The kit of 46, wherein said means for detecting the presence or absence of the mutant TRIM5α polypeptide of any one of 1 to 24 comprises an antibody specifically recognizing said mutant polypeptide.

49. The kit of 47, wherein said means for detecting the presence or absence of the nucleic acid of any one of 25 to 27 comprises an oligonucleotide specifically binding to said nucleic acid.

50. A kit for preventing or treating a lentivirus infection in a subject, comprising (i) the mutant TRIM5α polypeptide of any one of 1 to 24; (ii) the nucleic acid of any one of 25 to 27; (iii) the vector of 28 or 29; (iv) the cell of any one of 30 to 32 and/or (v) the composition of 33.

51. A method for increasing the resistance of a cell to lentivirus infection, said method comprising increasing the expression of the (i) the mutant TRIM5α polypeptide of any one of 1 to 24; and/or (ii) the nucleic acid of any one of 25 to 27, in said cell.

52. The method of 51, wherein said lentivirus infection is human immunodeficiency virus (HIV) infection.

53. Use of the (i) the mutant TRIM5α polypeptide of any one of 1 to 24; and/or (ii) the nucleic acid of any one of 25 to 27 for increasing the resistance of a cell to lentivirus infection.

54. Use of the (i) the mutant TRIM5α polypeptide of any one of 1 to 24; and/or (ii) the nucleic acid of any one of 25 to 27 for the preparation of a medicament for increasing the resistance of a cell to lentivirus infection.

55. The use of 53 or 54, wherein said lentivirus infection is human immunodeficiency virus (HIV) infection.

56. An agent selected from: (i) the mutant TRIM5α polypeptide of any one of 1 to 24; (ii) the nucleic acid of any one of 25 to 27; (iii) the vector of 28 or 29; and/or (iv) the composition of 33, for increasing the resistance of a cell to lentivirus infection.

57. The agent of 56, wherein said lentivirus infection is human immunodeficiency virus (HIV) infection.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1 shows a random mutagenesis screen of TRIM5α$_{hu}$.

FIG. 2 shows a site-directed mutagenesis of TRIM5α$_{hu}$.

FIG. 3 shows the effect of Arg332 and Arg335 mutations on the anti-retroviral activity of TRIM5α$_{hu}$. TE671 cells expressing wild-type and mutant TRIM5α$_{hu}$ or transduced with the empty parental vector were challenged with multiple doses of the indicated VSV G-pseudotyped, GFP-expressing retroviral vectors. The percentages of GFP-positive cells were assessed by flow cytometry two days later.

FIG. 5 shows inhibition of HIV-1 spreading replication by TRIM5α$_{hu}$ mutants.

FIG. 6 shows the nucleotide and amino acid sequences of human TRIM5α. FIGS. 6A and 6B show the nucleotide (SEQ ID NO: 23; GenBank Accession #NM_033034) and amino acid (SEQ ID NO: 24; GenBank Accession #NP_149023.1) sequences of native (wild-type) human TRIM5α, with residue 335 in bold. FIG. 6C shows the amino acid sequence of human TRIM5α comprising a mutation at position 335 (SEQ ID NO: 25), FIG. 6D shows the amino acid sequence of human TRIM5α comprising mutations at positions 332 and 335 (SEQ ID NO: 26), and FIG. 6E shows the amino acid sequence of human TRIM5α comprising a mutation at position 330 (SEQ ID NO: 30);

FIG. 7 shows the nucleotide (FIG. 7A; SEQ ID NO: 27; GenBank Accession #DQ842021) and amino acid (FIG. 7B; SEQ ID NO: 28; GenBank Accession #ABG67967) sequences of rhesus macaque (*Macaca mulatta*) TRIM5α; and FIGS. 8A and 8B show the effect of various mutations in the PRYSPRY domain identified by a mutagenesis screening on the anti-retroviral activity of TRIM5α$_{hu}$. TE671 cells expressing wild-type and mutant TRIM5α$_{hu}$ or transduced with the empty parental vector were challenged with the HIV-1$_{TRIP-CMV-GFP}$ vector. The percentages of GFP-positive cells were assessed by flow cytometry two days later.

DISCLOSURE OF INVENTION

Figure 1A:
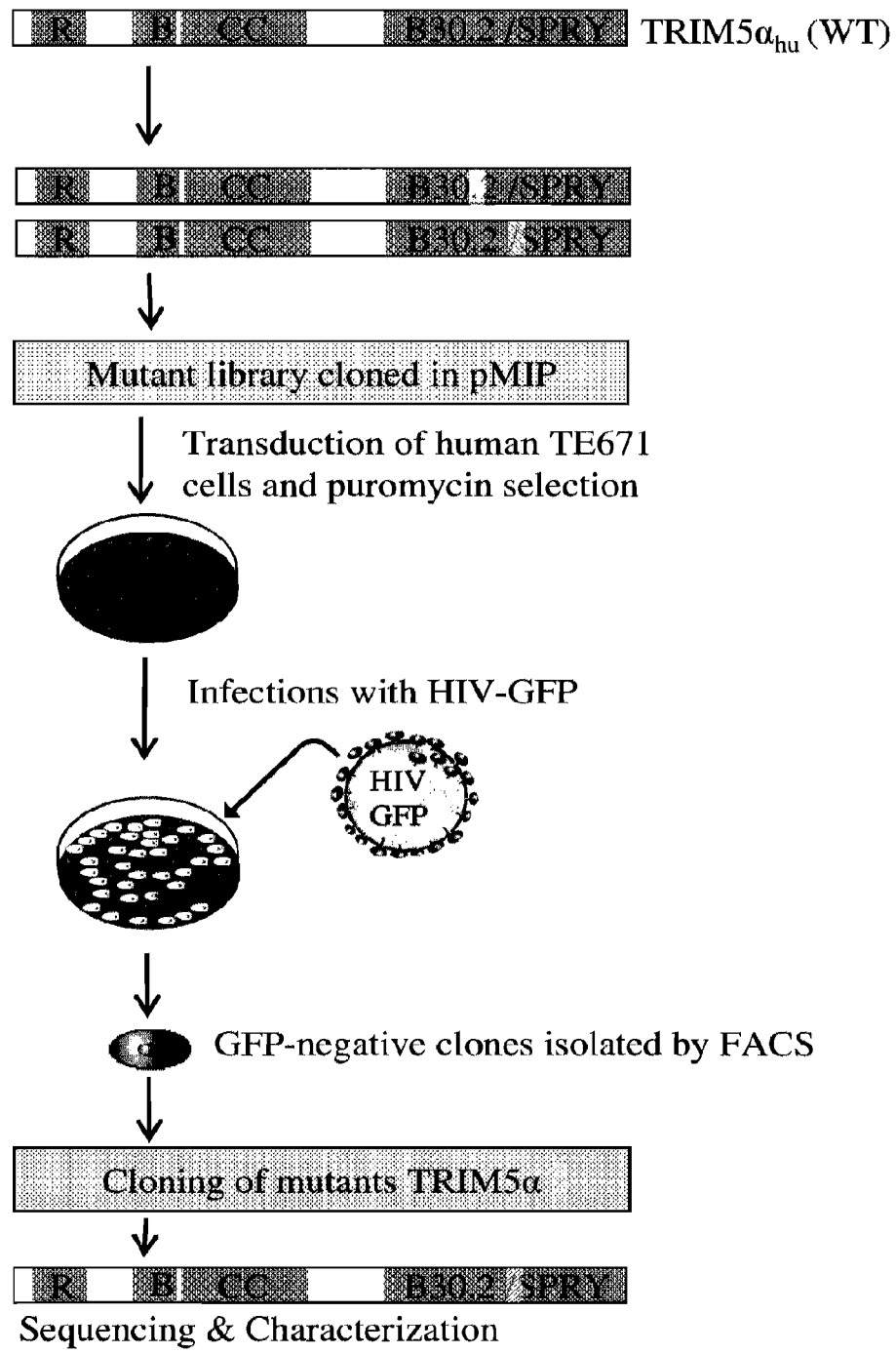
FIG. 1A shows an outline of the protocol used. PCR-based mutagenesis was confined to the B30.2/SPRY domain of TRIM5α$_{hu}$ and followed by a FACS-based functional assay to isolate cells resistant to HIV-1 infection.

Described herein are mutant or modified forms of TRIM5α, and uses thereof.

TRIM (tripartite motif) proteins form a family of dozens of members, most of them comprising a RING domain (spanning about residues 15-59 in human TRIM5α), a B-box domain (spanning about residues 90-132 in human TRIM5α) and a Coiled-coil domain (spanning about residues 130-241 in human TRIM5α), collectively referred to as RBCC domains. In addition to the RBCC motif, TRIM5α contains a C-terminal B30.2 (also called SPRY or PRYSPRY) domain spanning about residues 281-493 in human TRIM5α, the most variable domain of the protein (it contains 4 highly variable regions labeled v1 to v4, as depicted in FIG. 1D), that play a role in restriction specificity (Perez-Caballero et al., 2005. *J Virol* 79:8969-78). TRIM5α was isolated in 2004 as the factor governing the resistance of rhesus macaque monkeys to transduction by HIV-1 vectors. Restriction by TRIM5α is initiated by physical recognition of incoming retroviruses by TRIM5α proteins (Sebastian, S., and J. Luban. 2005. *Retrovirology* 2:40; Stremlau, M., et al., 2006. *Proc Natl Acad Sci USA* 103:5514-9), which occurs within the first hours following virus entry (Perez-Caballero, D., et al., 2005. *J Virol* 79:15567-72) and involves determinants present in the N-terminal domain of the capsid proteins which constitute the retroviral outer core structure (Hatziioannou, T., et al., 2004. *J Virol* 78:6005-12; Ikeda, Y., et al., 2004. *J Virol* 78:11816-22; Owens, C. M., et al., 2004. *J Virol* 78:5423-37). Following this initial contact, progression of the retroviral life cycle is impeded through several mechanisms. TRIM5α interferes with the uncoating process of retroviruses, thus preventing successful reverse transcription and transport to the nucleus of the viral genome. The proteasome is also involved and causes a decrease in retroviral cDNA accumulation in acutely infected cells (Anderson, J. L. et al., 2006. *J Virol* 80:9754-60). TRIM5α proteins can seemingly self-ubiquitinate (Diaz-Griffero, F. et al., 2006. *Virology* 349: 300-15; Yamauchi, K., et al., 2008. *FEBS J* 275:1540-55) and are rapidly degraded by the proteasome upon exposure to a restriction-sensitive virus (Rold, C. J., and C. Aiken. 2008. *PLoS Pathog* 4: e1000074). Lastly, TRIM5α interferes with the transport of post-entry retroviral complexes toward the nucleus, and this antiviral activity is independent from the one involving the proteasome (Campbell, E. M. et al., 2008. *J Cell Biol* 180:549-61; Wu, X., et al., 2006. *Proc Natl Acad Sci USA* 103:7465-70).

Correspondence of amino acid positions described herein is frequently expressed in terms of the positions of the amino acids of the form of wild-type (or native) human TRIM5α set forth in SEQ ID NO: 24 (FIGS. 6A and 6B). For example, the positions correspond to one or more of the amino acid arginine (Arg or R) set forth at positions 332 and 335 in FIGS. 6A and 6B, or the amino acid glycine set forth at position 330 in SEQ ID NO: 24 (FIGS. 6A and 6B). A "mutant" or "modified" TRIM5α polypeptide as used herein refers to a polypeptide having TRIM5α activity, i.e., capable of recognizing motifs within the capsid proteins of retroviruses and interfering with viral replication (e.g., by interference with the uncoating process, modulation of proteasome-mediated degradation, and/or interference with the transport of post-entry retroviral complexes toward the nucleus), the polypeptide having a different amino acid from the wild-type protein at one or more positions, for example at position(s) 324, 328, 330, 333, 335, 336 and/or 337, as described more fully in the specification, in relation to the wild-type protein of SEQ ID NO: 24 (FIGS. 6A and 6B). Therefore, amino acid numbering can be shifted in situations where the residues corresponding to the wild-type arginine residues noted herein are within a polypeptide of the present invention having TRIM5α activity, the polypeptide having for example more or fewer amino acids N-terminal to the region where these residues reside, relative to the wild-type, thereby resulting in different amino acid numbering relative to the positions of wild-type TRIM5α. As such, a position(s) within a polypeptide of the present invention may correspond to the wild-type TRIM5α arginine positions noted herein, but have different position numbers relative to the wild-type depending on their location within the polypeptide.

The present inventors have shown that mutant TRIM5α polypeptides comprising a mutation at a residue corresponding to residue 324, 328, 330, 333, 335, 336 and/or 337 of the native human TRIM5α polypeptide inhibit lentivirus replication.

Accordingly, in a first aspect, the present invention provides a TRIM5α mutant polypeptide, in which the amino acid residue corresponding to lysine (Lys or K) at position 324, isoleucine (Ile or I) at position 328, glycine (Gly or G) at position 330, glycine (Gly or G) at position 333, arginine (Arg or R) at position 335, tyrosine (Tyr or Y) at position 336 and/or glutamine (Gln or Q) at position 337 in SEQ ID NO: 24 (FIGS. 6A and 6B) has been altered compared with wild-type/native human TRIM5α. Also provided is a nucleic acid encoding said polypeptide. The TRIM5α mutant confers resistance to lentivirus infection (e.g., HIV infection), and more particularly a higher resistance relative to wild-type human TRIM5α. In an embodiment, the above-mentioned TRIM5α mutant polypeptide is a human TRIM5α mutant polypeptide. In an embodiment, the above-mentioned mutant does not have one of the following mutations: R335L or R335F. In an embodiment, the above-mentioned mutant has at least one of the following amino acid mutations: R335G, R335D, R335E, R335K, or a deletion of R335 (ΔR335). In an embodiment, the above-mentioned TRIM5α mutant polypeptide comprises the amino acid sequence of FIG. 6C (SEQ ID NO: 25). In an embodiment, the above-mentioned mutant has at least one of the following amino acid mutations: G330E or G330D. In an embodiment, the above-mentioned TRIM5α mutant polypeptide comprises the amino acid sequence of FIG. 6E (SEQ ID NO: 30). In other embodiments, the mutant TRIM5α polypeptide comprises a substitution with a Gln residue at position 324, a substitution with a Ser residue at position 328, a substitution with a Val residue at position 333, a substitution with a Cys residue at position 336, and/or a substitution with a Pro residue at position 337.

In another embodiment, the TRIM5α mutant polypeptide further comprises a further mutation, i.e. in which the amino acid residue corresponding to arginine (Arg or R) at position 332 in SEQ ID NO: 24 (FIGS. 6A and 6B) has been altered compared with wild-type/native human TRIM5α. In an embodiment, the above-mentioned TRIM5α mutant polypeptide comprises an arginine to glycine (R332G) substitution.

In a further embodiment, the above-mentioned TRIM5α mutant polypeptide comprises the sequence of SEQ ID NO: 26 (FIG. 6D).

In embodiments, the mutant TRIM5α polypeptide comprises any combination of the above-noted mutations (i.e., comprising two or more of the above-noted mutations at positions 324, 328, 330, 333, 335, 336 and/or 337), e.g., mutations at positions 330 and 332, mutations at positions 330 and 335, mutations at positions 332 and 335, mutations at positions 330, 332 and 335, etc. In an embodiment, the mutant TRIM5α polypeptide comprises arginine to glycine substitutions at positions 332 and 335 (R332G/R335G). In another embodiment, the mutant TRIM5α polypeptide comprises a glycine to glutamic acid substitution at position 330 and arginine to glycine substitution at positions 332 and 335 (G330E/R332G/R335G).

The invention further provides a variant or fragment of the above-noted mutant TRIM5α polypeptide (e.g., a truncated form of the above-mentioned mutant TRIM5α polypeptide, a fusion or chimeric polypeptide comprising the above-mentioned mutant TRIM5α polypeptide, etc.), the variant or fragment comprising the above-noted mutations at positions corresponding to positions 324, 328, 330, 333, 335, 336 and/or 337, or at positions 335 and 332, noted above, the variant or fragment further having an activity similar to that of the above-noted mutant TRIM5α polypeptide. Such a variant may for example be substantially identical to a polypeptide described herein (e.g., any of FIG. 6C, 6D or 6E).

The mutant TRIM5α polypeptides of the present invention may also be in the form of a fusion protein comprising a polypeptide described herein having TRIM5α activity or a variant or fragment thereof and a further polypeptide sequence, for example incorporating a tag which may for example facilitate purification or detection of the mutant TRIM5α polypeptide (e.g., a His$_6$-tag, a FLAG tag or a GST-tag).

In an embodiment, the above-mentioned mutant TRIM5α polypeptide confers a higher/better resistance to lentivirus infection (e.g., shows higher inhibition of lentivirus replication) as compared to wild-type/native human TRIM5α polypeptide. In an embodiment, the above-mentioned mutant TRIM5α polypeptide confers a resistance to lentivirus infection that is at least about 2-fold higher, in further embodiments at least about 3-fold, 4-fold, 5-fold, 6-fold, 7-fold, 8-fold, 9-fold, 10-fold, 15-fold, 20-fold or 25-fold higher, relative to wild-type/native human TRIM5α polypeptide. In an embodiment, the above-mentioned resistance to lentivirus infection is measured using the assay described below.

In a further aspect, the present invention provides an isolated nucleic acid comprising a sequence encoding any of the above-mentioned polypeptides, or a homolog, fragment or variant thereof. The nucleic acid of the present invention includes those sequences that, because of the degeneracy of the genetic code, encode the amino acid sequence of any of the TRIM5α mutant polypeptide described herein (e.g., any of FIG. 6C, 6D or 6E).

Mutagenesis can be performed utilizing any one of several techniques known to those of skill in the art (see for example, Jeff Braman, in In Vitro Mutagenesis Protocols, 2$^{nd}$ edition (2002), Humana Press, 304 pages), for example using an overlap extension PCR technique, as described below (see also Ho, S, N. et al., 1989. Gene 77:51-9). Moreover, kits for site-directed mutagenesis are commercially available, such as Quickchange™ Site-Directed Mutagenesis Kit from STRATAGENE®, GeneTailor™ Site-Directed Mutagenesis System from INVITROGEN®, Altered Sites™ in vitro Mutagenesis System from PROMEGA®. Also, the mutagenesis may be performed randomly, for example using a commercially available kit (Diversify™ PCR Random Mutagenesis kit, CLONTECH®), followed by a selection of the mutants have the desired activity, as described below.

The term "TRIM5α activity" as used herein refers to, for example, the reduction of retrovirus (e.g., lentivirus) replication. The activity of the mutant form of TRIM5α may for example be assessed in vitro by determining the replication of a given retrovirus in cells comprising/expressing the mutant, for example using the assay described in the examples below.

In another aspect of the invention, an isolated nucleic acid, for example a nucleic acid sequence encoding the above-mentioned TRIM5α mutant, or homolog, fragment or variant thereof, may further be incorporated into a vector, such as a recombinant expression vector (e.g., a eukaryotic expression vector, a viral expression vector). In an embodiment, the vector comprises transcriptional regulatory sequences or a promoter operably-linked to a nucleic acid comprising a sequence capable of encoding a mutant polypeptide of the invention. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequence. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous. "Transcriptional regulatory sequences" or "transcriptional regulatory elements" are generic terms that refer to DNA sequences, such as initiation and termination signals, enhancers, and promoters, splicing signals, polyadenylation signals, etc., which induce or control transcription of protein coding sequences with which they are operably-linked.

Various genes and nucleic acid sequences of the invention may be recombinant sequences. Further, polypeptides or proteins of the invention may also be recombinant. The term "recombinant" means that something has been recombined, so that when made in reference to a nucleic acid the term refers to a molecule that is comprised of nucleic acid sequences that are joined together or produced by means of molecular biological techniques. The term "recombinant" when made in reference to a protein or a polypeptide refers to a protein or polypeptide molecule, which is expressed using a recombinant nucleic acid construct created by means of molecular biological techniques. The term "recombinant" when made in reference to a genetic composition refers to a gamete or progeny or cell or genome with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

In accordance with the present invention, an isolated nucleic acid molecule, is a nucleic acid molecule that has been removed from its natural milieu (i.e., that has been subjected to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecules can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

"Homology" and "homologous" refers to sequence similarity between two polypeptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid or polypeptide sequence is "homologous" to another sequence if the two sequences are substantially identical and the functional activity of the sequences is conserved (as used herein, the term 'homologous' does not infer evolutionary relatedness). Two nucleic acid or polypeptide sequences are considered "substantially identical" if, when optimally aligned (with gaps permitted), they share at least about 50% sequence similarity or identity and/or if the sequences share defined functional motifs. In alternative embodiments, sequence similarity in optimally aligned substantially identical sequences may be at least 60%, 70%, 75%, 80%, 85%, 90%, 95%, 96%, 97%, 98% or 99% with any of the polypeptide or nucleic acid sequences of the invention. As used herein, a given percentage of homology between sequences denotes the degree of sequence identity in optimally aligned sequences. An "unrelated" or "non-homologous" sequence shares less than 40% identity, though preferably less than about 25% identity, with any of the polypeptide or nucleic acid sequences of the invention. "Substantially complementary" nucleic acids are nucleic acids in which the complement of one molecule is substantially identical to the other molecule.

Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215: 403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al., (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al., (eds), 1989, supra). Hybridization conditions may be modified in accordance with known methods depending on the sequence of interest (see Tjjssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

The recombinant expression vector of the present invention can be constructed by standard techniques known to one of ordinary skill in the art and found, for example, in Sambrook et al. (1989) in Molecular Cloning: A Laboratory Manual; and Sambrook and Russell (2001) Molecular Cloning: A Laboratory Manual ($3^{rd}$ edition; Cold Spring Harbor Laboratory). A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation. In addition, the vectors of the present invention may comprise a sequence of nucleotides for one or more restriction endonuclease sites. Coding sequences such as for reporter genes are well known to persons skilled in the art. In an embodiment, the vector further comprises one or more gene(s) of interest.

A recombinant expression vector comprising a nucleic acid sequence of the present invention may be introduced into a cell, e.g., a host cell, which may include a living cell capable of expressing the protein coding region from the defined recombinant expression vector. Accordingly, the invention also provides host cells containing the nucleic acid or recombinant expression vector of the invention. The terms "host cell" and "recombinant host cell" are used interchangeably herein. Such terms refer not only to the particular subject cell, but also to the progeny or potential progeny of such a cell. Because certain modifications may occur in succeeding generations due to either mutation or environmental influences, such progeny may not, in fact, be identical to the parent cell, but are still included within the scope of the term as used herein.

Vectors can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), Sambrook and Russell (supra) and other laboratory manuals. Methods for introducing nucleic acids into mammalian cells in vivo are also known, and may be used to deliver the vector DNA of the invention to a subject for gene therapy.

The above-mentioned nucleic acid may be delivered to cells in vivo using methods well known in the art such as direct injection of DNA, receptor-mediated DNA uptake, viral-mediated transfection or non-viral transfection and lipid-based transfection, all of which may involve the use of gene therapy vectors. Direct injection has been used to introduce naked DNA into cells in vivo (see e.g., Acsadi et al. (1991) *Nature* 332:815-818; Wolff et al. (1990) *Science* 247: 1465-1468). A delivery apparatus (e.g., a "gene gun") for injecting DNA into cells in vivo may be used. Such an apparatus may be commercially available (e.g., from BIORAD®). Naked DNA may also be introduced into cells by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963-967; and U.S. Pat. No. 5,166, 320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126).

Defective retroviruses are well characterized for use as gene therapy vectors (for a review see Miller, A. D. (1990) *Blood* 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psiCrip, psiCre, psi2 and psiAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al., (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. immunol.* 150: 4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

For use as a gene therapy vector, the genome of an adenovirus may be manipulated so that it encodes and expresses a nucleic acid compound of the invention (e.g., a nucleic acid encoding a TRIM5α variant), but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al., (1992) *Proc. Natl. Acad. Sci. USA* 89:2581-2584).

Adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle (Muzyczka et al. *Curr. Topics in Micro. and Immunol.* (1992) 158:97-129). AAV may be used to integrate DNA into non-dividing cells (see for example Flotte et al., (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). An AAV vector such as that described in Tratschin et al. (1985) *Mol. Cell. Biol.* 5:3251-3260 may be used to introduce DNA into cells (see for example Hermonat et al. (1984) *Proc. Natl. Acad. Sci. USA* 81:6466-6470; Tratschin et al. (1985) *Mol. Cell. Biol.* 4:2072-2081; Wondisford et al., (1988) *Mol. Endocrinol.* 2:32-39; Tratschin et al. (1984) J. Virol. 51:611-619; and Flotte et al., (1993) *J. Biol. Chem.* 268:3781-3790). Lentiviral gene therapy vectors may also be adapted for use in the invention.

In an embodiment, the above-mentioned expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235-275), such as the promoters of T cell receptors (Winoto and Baltimore (1989) *EMBO J.* 8:729-733) and immunoglobulins (Banerji, et al. (1983) *Cell* 33:729-740; Queen and Baltimore (1983) Cell 33:741-748).

General methods for gene therapy are known in the art. See for example, U.S. Pat. No. 5,399,346 by Anderson et al., A biocompatible capsule for delivering genetic material is described in PCT Publication WO 95/05452 by Baetge et al. Methods of gene transfer into hematopoietic cells have also previously been reported (see Clapp, D. W., et al., Blood 78: 1132-1139 (1991); Anderson, *Science* 288:627-9 (2000); and Cavazzana-Calvo et al., *Science* 288:669-72 (2000)).

In an embodiment, the above-mentioned cell (host cell) is a bone marrow cell, such as a stem cell, in a further embodiment a pluripotent stem cell, in a further embodiment a multipotent stem cell, such as a hematopoietic stem cell (HSC).

As used herein, the term "hematopoietic stem cells (HSC)" means a population of primitive progenitor cells which can provide long term reconstitution of both myeloid and lymphoid cell lineages in a host when introduced thereinto. The hematopoietic stem cell, which may be isolated from bone marrow, blood, cord blood, fetal liver and yolk sac, is the progenitor cell that generates blood cells or following transplantation reinitiates multiple hematopoietic lineages and can reinitiate hematopoiesis for the life of a recipient. When transplanted into lethally irradiated subjects (e.g., animals, such as humans), hematopoietic stem cells can repopulate the erythroid, neutrophil-macrophage, megakaryocyte and lymphoid hematopoietic cell pool. Where the stem cells to be provided to a subject in need of such treatment are hematopoietic stem cells, they are most commonly obtained from the bone marrow of the subject (autologous) or a compatible donor (heterologous). Bone marrow cells can be easily isolated using methods known in the art.

Hematopoietic stem cells can also be obtained from blood products. A "blood product" as used in the present invention defines a product obtained from the body or an organ of the body containing cells of hematopoietic origin. Such sources include unfractionated bone marrow, umbilical cord, peripheral blood, liver, thymus, lymph and spleen. It will be apparent to those of ordinary skill in the art that all of the aforementioned crude or unfractionated blood products can be enriched for cells having "hematopoietic stem cell" characteristics in a number of ways. For example, the blood product can be depleted from the more differentiated progeny. The more mature, differentiated cells can be selected against, via cell surface molecules they express. Unfractionated blood products can be obtained directly from a donor or retrieved from cryopreservative storage.

In another aspect, the present invention provides a cell population (e.g., a T cell population), organ or tissue expressing the above-mentioned mutant TRIM5α polypeptide.

In another aspect, the present invention provides a transgenic non-human animal (e.g., a non-human mammal) comprising the above-mentioned mutant TRIM5α polypeptide/nucleic acid.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., *Proc. Natl. Acad. Sci. USA* 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes. In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912). In other embodiments, the developing non-human embryo can be cultured in vitro to the blastocyst stage. During this time, the blastomeres can be targets for retroviral infection (Janenich, *Proc. Natl. Acad. Sci. USA* 73:1260, 1976). Efficient infection of the blastomeres is obtained by enzymatic treatment to remove the zona pellucida (Hogan et al., in Manipulating the Mouse Embryo, Cold Spring Harbor Laboratory Press, Cold Spring Harbor, N.Y. 1986). The viral vector system used to introduce the transgene is typically a replication-defective retrovirus carrying the transgene (Jahner et al., *Proc. Natl. Acad. Sci. USA* 82:6927, 1985). Transfection is easily and efficiently obtained by culturing the blastomeres on a monolayer of virus-producing cells (Stewart et al., *EMBO J.*, 6:383, 1987). Alternatively, infection can be performed at a later stage. Virus or virus-producing cells can be injected into the blastocoele (Jahner et al., Nature 298: 623, 1982). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra, 1982). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International publication No. WO 90/08832, and Haskell and Bowen, *Mol. Reprod. Dev.*, 40: 386, 1995).

In other embodiments, the transgene is introduced into embryonic stem cells and the transfected stem cells are utilized to form an embryo. ES cells are obtained by culturing pre-implantation embryos in vitro under appropriate conditions (Evans et al., *Nature* 292:154, 1981; Bradley et al., *Nature* 309:255, 1984; Gossler et al., *Proc. Acad. Sci. USA* 83:9065, 1986; and Robertson et al., *Nature* 322:445, 1986). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (See, Jaenisch, *Science* 240:1468, 1988). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396.

In another aspect, the present invention provides an antibody specifically recognizing the above-mentioned mutant TRIM5α polypeptide. Specifically recognizing as used herein means that the antibody specifically binds to (interacts with) a mutant TRIM5α polypeptide and displays no substantial binding or lower binding to other naturally occurring proteins, and more particularly to native/wild-type TRIM5α polypeptides. The term antibody or immunoglobulin is used in the broadest sense, and covers monoclonal antibodies (including full-length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions (VH, VH-VH), anticalins, PepBodies, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody as used herein encompasses polyclonal, monoclonal antibodies and antibody variants such as single-chain antibodies, humanized antibodies, chimeric antibodies and immunologically active fragments of antibodies (e.g., Fab and Fab' fragments) which inhibit or neutralize their respective interaction domains in Hyphen and/or are specific thereto.

Polyclonal antibodies are preferably raised in animals by multiple subcutaneous (s.c.), intravenous (i.v.) or intraperitoneal (i.p.) injections of the relevant antigen (e.g., a mutant TRIM5α polypeptide or a fragment thereof comprising the above-mentioned mutations(s)) with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and are different alkyl groups.

Animals may be immunized against the antigen (e.g., a mutant TRIM5α polypeptide or a fragment thereof comprising the above-mentioned mutations(s)), immunogenic conjugates, or derivatives by combining the antigen or conjugate (e.g., 100 µg for rabbits or 5 µg for mice) with 3 volumes of Freund's complete adjuvant and injecting the solution intradermally at multiple sites. One month later the animals are boosted with the antigen or conjugate (e.g., with ⅕ to ⅒ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., *Nature*, 256: 495 (1975), or may be made by recombinant DNA methods (e.g., U.S. Pat. No. 6,204,023). Monoclonal antibodies may also be made using the techniques described in U.S. Pat. Nos. 6,025, 155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In another aspect, the present invention provides a composition (e.g., a pharmaceutical composition) comprising the (i) above-mentioned mutant TRIM5α polypeptide; (ii) the above-mentioned nucleic acid; (iii) the above-mentioned vector; and/or (iv) the above-mentioned cell. In an embodiment, the composition further comprises a carrier, diluent and/or excipient (e.g., a pharmaceutically acceptable carrier, diluent and/or excipient). As used herein "pharmaceutically acceptable carrier" or "excipient" includes any and all solvents, buffers, dispersion media, coatings, antibacterial and antifungal agents, isotonic and absorption delaying agents, and the like that are physiologically compatible. The carrier can be suitable, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art (Rowe et al., Handbook of pharmaceutical excipients, 2003, 4$^{th}$ edition, Pharmaceutical Press, London UK). Except insofar as any conventional media or agent is incompatible with the active compound, use thereof in the pharmaceutical compositions of the invention is contemplated.

The composition may also contain more than one active compound for the particular indication being treated, preferably those with complementary activities that do not adversely affect each other. It may be desirable to use the above-mentioned composition in addition to one or more agents that may be used to prevent or treat the disorder in question (e.g., an antiretroviral drug such as reverse transcriptase inhibitors, protease inhibitors, integrase inhibitors, immunomodulators, vaccines, etc.). The above-mentioned agents may be formulated in a single composition or in several individual compositions which may be co-administered in the course of the treatment.

Formulations to be used for in vivo administration are preferably sterile. This is readily accomplished, for example, by filtration through sterile filtration membranes.

In another aspect, the present invention provides a method (in vivo or in vitro) for increasing the resistance of a cell to lentivirus infection (e.g., for rendering a cell resistant to lentivirus infection) comprising inducing or increasing the expression of the above-mentioned mutant TRIM5α polypeptide in said cell, for example by introducing the above-mentioned nucleic acid or vector into the cell.

In another aspect, the present invention provides a method for preventing or treating a lentivirus infection in a subject in need thereof, said method comprising administering to said subject in need thereof an effective amount of (i) the above-mentioned mutant TRIM5αpolypeptide; (ii) the above-mentioned nucleic acid; (iii) the above-mentioned vector; (iv) the above-mentioned cell and/or (v) the above-mentioned composition.

In an embodiment, the above-mentioned method comprises (a) introducing the above-mentioned nucleic acid and/or the above-mentioned vector into a donor cell; and (b) administering an effective amount of the donor cell to said subject.

In another aspect, the present invention provides a use of (i) the above-mentioned mutant TRIM5α polypeptide; (ii) the above-mentioned nucleic acid; (iii) the above-mentioned vector; (iv) the above-mentioned cell and/or (v) the above-mentioned composition, as a medicament.

In another aspect, the present invention provides a use of (i) the above-mentioned mutant TRIM5α polypeptide; (ii) the above-mentioned nucleic acid; (iii) the above-mentioned vector; (iv) the above-mentioned cell and/or (v) the above-mentioned composition; for preventing or treating a lentivirus infection in a subject.

In another aspect, the present invention provides a use of (i) the above-mentioned mutant TRIM5α polypeptide; (ii) the above-mentioned nucleic acid; (iii) the above-mentioned vector; (iv) the above-mentioned cell and/or (v) the above-mentioned composition; for the preparation of a medicament for preventing or treating a lentivirus infection in a subject.

In an embodiment of the invention, the above-mentioned donor cell, such as a stem cell (e.g., HSC), is transformed/transfected ex vivo and then transplanted into the subject. In an embodiment such transplantation is autologous, whereby the donor cell is obtained from the subject, transformed ex vivo and returned to the same patient. In another embodiment, such transplantation is allogeneic, whereby the donor cell is obtained from a genetically non-identical member of the same species as the recipient, transformed ex vivo and injected/infused into the recipient.

Lentivirus infection refers to an infection by a virus of the Retroviridae family that comprises non-oncogenic retroviruses that typically produce multi-organ diseases characterized by long incubation periods and persistent/chronic infection. Lentiviruses contain open reading frames (ORFs) between the pol and env genes and in the 3' env region. Five serogroups are recognized, reflecting the mammalian hosts with which they are associated (bovine, equine, feline, ovine/caprine and primate). In an embodiment, the above-mentioned lentivirus infection is human immunodeficiency virus (HIV) infection, in a further embodiment, HIV-1 infection, in a further embodiment, HIV-2 infection.

In an embodiment, the above-mentioned treatment comprises the use/administration of more than one (i.e., a combination of) active agents. The combination of prophylactic/therapeutic agents and/or compositions of the present invention may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) of the present invention is used/administered in combination with one or more agent(s) currently used to prevent or treat the disorder in question, for example an anti-retroviral agent.

The amount of the pharmaceutical composition (e.g., a composition comprising the above-mentioned polypeptide, nucleic acid, vector or cell) which is effective in the prevention and/or treatment of a particular disease, disorder or condition (e.g., lentivirus infection, lentivirus-related disease) will depend on the nature and severity of the disease, the chosen prophylactic/therapeutic regimen, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a patient, in the context of the present invention should be sufficient to effect a beneficial prophylactic and/or therapeutic response in the patient over time. The size of the dose also will be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

In another aspect, the present invention provides packages or kits comprising the above-mentioned polypeptide, nucleic acid, cell or composition together with a container. The kit may further comprises instructions for their use for preventing or treating lentivirus infection or disease. Kits can also provide buffers, excipients, as well as means for administering the polypeptide, nucleic acid, cell or composition to a subject.

The terms "treating" or "treatment" as used herein refers to the application or administration of the above-mentioned mutant TRIM5α polypeptide, nucleic acid, cell or composition, to a subject having a lentivirus infection or symptom of infection and where the purpose is to cure, heal, alleviate, relieve, alter, remedy, ameliorate, improve, or affect the infection or any associated symptoms of the infection. The terms "preventing" or "prevention" as used herein refers to the application or administration of the above-mentioned mutant TRIM5αpolypeptide, nucleic acid, cell or composition, to a subject that has been exposed to a lentivirus, or that is at risk of being exposed to the infection, or has a predisposition toward development of a lentivirus infection, where the purpose is to inhibit or stop the development of infection or associated symptoms, or to delay the onset or development of the infection or associated symptoms.

In another aspect, the present invention provides a method (in vivo or in vitro) for determining whether a subject has an increased resistance to lentivirus infection, said method comprising; determining, in a biological sample from said subject, the presence or absence (i) the above-mentioned mutant TRIM5α polypeptide; and/or (ii) the above-mentioned nucleic acid; wherein the presence of said mutant TRIM5α polypeptide and/or nucleic acid is indicative that said subject has an increased resistance to lentivirus infection.

In another aspect, the present invention provides a kit for determining whether a subject has an increased resistance to lentivirus infection, said kit comprising means for detecting the presence or absence of (i) the above-mentioned mutant TRIM5α polypeptide; and/or (ii) the above-mentioned nucleic acid encoding a mutant TRIM5α polypeptide; together with a container. In an embodiment, such a kit may further comprise instructions for determining whether a subject has an increased resistance to lentivirus infection. "Increased resistance" as used herein refers to a better resistance (or decreased susceptibility/predisposition) to lentivirus infection as compared to a subject expressing a wild-type TRIM5α polypeptide.

In an embodiment, the above-mentioned means for detecting the presence or absence of the mutant TRIM5α polypeptide comprises a ligand (e.g., an antibody) specifically recognizing said mutant polypeptide (i.e. binding preferentially to the mutant TRIM5αpolypeptide relative to a wild-type TRIM5α polypeptide). Such ligand may be labelled (e.g., with a fluorescent moiety) so as to facilitate the detection of the complex between the ligand and the mutant TRIM5α polypeptide. In an embodiment, such a kit may further comprises reagents (buffers, enzymes) used for polypeptide detection, such as enzyme-linked immunosorbent assay (ELISA) or flow cytometry reagents.

In an embodiment, the above-mentioned means for detecting the presence or absence of a nucleic acid encoding a mutant TRIM5α polypeptide comprises an oligonucleotide (a probe, a primer) binding (e.g., under stringent conditions) to said nucleic acid. Such oligonucleotide may be labelled (e.g., with a fluorescent or radioactive moiety) so as to facilitate the detection of the complex between the oligonucleotide and the nucleic acid. In an embodiment, the oligonucleotide binds to a region comprising the above-noted mutations, and thus binds preferentially to a mutant TRIM5α nucleic acid relative to a wild-type TRIM5α nucleic acid. In an embodiment, such a kit may further comprises reagents (buffers, enzymes) such as nucleic acid amplification reagents.

The determination can be carried out either as a DNA analysis according to well known methods, which include direct DNA sequencing of the normal and mutated TRIM5α gene, allele specific amplification using the polymerase chain reaction (PCR) enabling detection of either normal or mutated TRIM5α sequence, or by indirect detection of the normal or mutated TRIM5αgene by various molecular biology methods including, e.g., PCR-single stranded conformation polymorphism (SSCP)-method or denaturing gradient gel electrophoresis (DGGE). Determination of the normal or mutated TRIM5α gene can also be done by using restriction fragment length polymorphism (RFLP)-method, which is particularly suitable for genotyping large number of samples.

The determination can also be carried out at the level of RNA by analysing RNA expressed at tissue level using various methods. Allele specific probes can be designed for hybridization. Hybridization can be done, e.g., using Northern blot, RNase protection assay or in situ hybridization methods. RNA derived from the normal or mutated TRIM5α gene can also be analysed by converting tissue RNA first to cDNA and thereafter amplifying cDNA by an allele specific PCR-method and carrying out the analysis as for genomic DNA as mentioned above.

Alternatively, the determination can be carried out at the polypeptide level, for example using an immunoassay where a sample is contacted with an antibody capable of binding mutant or native TRIM5α polypeptide. Antibodies can be raised against normal or mutant TRIM5αpolypeptide. The production of antibodies can be done in experimental animals in vivo to obtain polyclonal antibodies or in vitro using cell lines to obtain monoclonal antibodies, as described above. In an embodiment, the antibody is an antibody specifically recognizing a mutant TRIM5αpolypeptide The term "subject" as used herein refers to any living organism. The term subject comprises, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. In embodiments, the subject is a mammal, including humans and non-human mammals. In a further embodiment, the subject is a human.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

MODE(S) FOR CARRYING OUT THE INVENTION

The present invention is illustrated in further details by the following non-limiting examples.

Example 1

Materials and Methods

Cells and Plasmids DNAs.

Human rhabdomyosarcoma TE671 cells and human embryonic kidney 293T cells were maintained in Dulbecco's Modified Eagle Medium (DMEM) supplemented with 10% fetal bovine serum and antibiotics at 37° C. Human T lymphoid SUP-T1 cells were cultured in RPMI 1640 supplemented with 10% fetal bovine serum and antibiotics at 37° C. All cell culture reagents were purchased from Hyclone.

pMIP-TRIM5$α_{hu}$, pMIP-TRIM5$α_{rh}$ and mutants of pMIP-TRIM5$α_{hu}$ all express C-terminal FLAG tagged versions of cDNAs (Sebastian, S. et al., 2006. *J Virol* 80:2051-4). pNL4-3, pNL-GFP, pMD-G, pCIG3N, pCIG3B, pCNCG, pΔR8.9, pTRIP$_{CMV\text{-}GFP}$, pCL-Eco, pROD$_{Nef\text{-}GFP}$, pSIV$_{mac\text{-}GFP}$, pONY3.1 and pONY8.0 have been previously described (Adachi, A. et al., 1986. *J Virol* 59:284-91; Berthoux, L. et al., 2005. *J Virol* 79:7883-8; Berthoux, L. et al. 2005. *Proc Natl Acad Sci USA* 102:14849-53; Berthoux, L. et al., 2004. *J Virol* 78:11739-50; Berthoux, L. et al., 2003. *J Virol* 77:3167-80; Mitrophanous, K. et al., 1999. *Gene Ther* 6:1808-18; Naviaux, R. K. et al., 1996. *J Virol* 70:5701-5; Reuter, S. et al., 2005. *Virology* 332:347-58; Zufferey, R. et al., 1997. *Nat Biotechnol* 15:871-5).

Production of Retroviral Vectors.

To produce replication-competent HIV-1, 293T cells plated at 80% confluency in 10-cm Petri dishes were transfected using polyethylenimine (PEI, Polysciences) with 10 μg of pNL4-3 or pNL-GFP, as previously described (Berube, J., et al., 2007. *Retrovirology* 4:68). All other retroviral vectors were pseudotyped with a vesicular stomatitis virus G (VSV G) protein. To produce HIV-1$_{TRIP-CMV-GFP}$, 293T cells were cotransfected with 10 μg of pTRIP$_{CMV-GFP}$, 10 μg of pΔR8.9 and 5 μg of pMD-G. To produce MLV vectors expressing GFP, 293T cells were similarly cotransfected with 10 μg of pCNCG, 10 μg of pCIG3 N or B, and 5 μg of pMD-G. HIV-2$_{ROD-GFP}$ and SIV$_{mac-GFP}$ vectors were produced by cotransfection of 10 μg of pROD$_{Nef-GFP}$ or pSIV$_{mac-GFP}$ respectively, and 5 μg of pMD-G. EIAV$_{GFP}$ were produced by cotransfection of 10 μg of pONY3.1, 10 μg of pONY8.0 and 5 μg of pMDG. Two days post-infection, the supernatants were collected, clarified by low speed centrifugation and stored in 1 ml aliquots at −80° C.

Library Construction.

Random mutations were introduced into the 830.2 domain of TRIM5α$_{hu}$ using the Diversify™ PCR Random Mutagenesis kit (CLONTECH®). Predefined experimental buffer conditions were tested in order to select the desired rate of one to two mutations per 600 bp. Buffer conditions #2 of the kit were used and consisted in an excess of dGTP combined with 160 μM of MnSO$_4$. Error-prone PCR was performed using 100 ng of pMIP-TRIM5α$_{hu}$ and the following primers: SPRY$_{fwd}$, 5'-ACAGATGTCCGACGCTACTGGGTT-3' (SEQ ID NO: 1) and TRIM5$_{rev}$, 5'-TCCTGAATTCTTACT-TATCGTCGTCATCCTTGTAATC-3' (SEQ ID NO: 2). DNA was amplified for 20 cycles (94° C., 15 sec; 60° C., 15 sec; 68° C., 1 min). The rest of TRIM5α$_{hu}$ was independently amplified with 20 units/ml of high fidelity replication Phusion™ enzyme from New England Biolabs (NEB) in 1× High Fidelity (HF) buffer. Each PCR reaction contained 1 ng of pMIPTRIM5α$_{hu}$, 0.2 mM of dNTP and 0.2 μM of each of the following oligonucleotides: TRIM5$_{fwd}$ (5'-GTTCCTC-GAGATGGCTTCTGGAATCCTGGTTAAT-3'; SEQ ID NO: 3) and SPRY$_{rev}$ (5'-AACCCAGTAGCGTCGGA-CATCTGT-3'; SEQ ID NO: 4). PCR was carried out for 25 cycles (98° C., 20 sec; 56° C., 20 sec; 72° C., 1 min). PCR products were cleaned of PCR reaction components using the QIAGEN QIAquick™ PCR purification kit. Aliquots (7 μl out of 50 μl) of each purified product were then mixed together to serve as templates in a second round of PCR, which used the TRIM5$_{fwd}$ and TRIM5$_{rev}$ oligonucleotides. DNA was amplified for 25 cycles (98° C., 20 sec; 56° C., 20 sec; 72° C., 1 min) using the Phusion™ enzyme. The resulting PCR fragment was gel-purified (Qiagen QiaQuick™ kit), digested with XhoI and EcoR1 and ligated to pMIP cut with the same enzymes. *E. coli* DH5α were transformed with the ligation products, yielding a library of 24,600 clones. A number of colonies were used to start small liquid cultures in order to prepare DNA for sequencing of individual clones. The other colonies were harvested and mixed together in liquid LB medium, and an aliquot of this resuspension was used to start a 125-ml overnight culture. Plasmid DNA was purified using the Qiagen Midiprep™ kit and used to produce MLV-derived retroviral vectors. For this, 10 μg of the library DNA were mixed with 10 μg of pCI-Eco and 5 μg of pMD-G and this mixture was transfected using Polyethylenimine (PEI) in 293T cells plated at 80% confluence in a 10-cm plate. Two days later, the supernatant of this plate was collected, aliquoted and frozen at −80° C. To express the library in human TE671 cells, cells were plated in 6-well plates at 250,000 cells per well and infected in duplicates with various amounts of the mutant-library MLV vectors. Two days later, cells were treated with 2 μg/ml puromycin. This concentration of puromycin is relatively high, allowing most of the non-transduced cells to die in less than 24 hours. The day after puromycin was added, mortality was estimated visually, and only cultures in which the virus dose led to no more than 10% transduced cells were maintained. These cells were pooled and cultured in 10-cm plates. For the functional selection, cells at about 10% confluence in 10-cm plates were challenged three (3) consecutive times with a preparation of HIV-1$_{TRIP-CMV-GFP}$. 5 ml of the undiluted GFP-expressing vector were used per plate and per infection, and infections were allowed to proceed for 16 h each. About a week later, cells were sorted by flow cytometry and GFP-negative cells (typically 1% of total intact cells) were plated at 1 cell/well in 96-well plates in DMEM-based culture medium supplemented with 10% conditioned medium (0.45 μm-filtered supernatant of confluent TE671 cells). The surviving clones were grown and challenged with HIV-1$_{TRIP-CMV-GFP}$ in 24-well plates as detailed below.

Site-Directed Mutagenesis.

Mutations were introduced by overlap extension PCR (Ho, S, N. et al., 1989. *Gene* 77:51-9). PCR reactions were performed using the High fidelity Phusion™ enzyme as detailed above. The following primers were used:

ΔR335$_{fwd}$:
(SEQ ID NO: 29)
5'-ACGAGGGACATACCAGACATTTGT-3'

ΔR335$_{rev}$:
(SEQ ID NO: 30)
5'-ATGTCTGGTATGTCCCTCGTGCCC-3'

R332G$_{fwd}$,
(SEQ ID NO: 5)
5'-ATATGGGGCAGGAGGGACAAGATAC-3'

R332G$_{rev}$,
(SEQ ID NO: 6)
5'-CTTGTCCCTCCTGCCCCATATATTA-3';

R335D$_{fwd}$,
(SEQ ID NO: 7)
5'-ACGAGGGACAGACTACCAGACATTTGT-3';

R335D$_{rev}$,
(SEQ ID NO: 8)
5'-ATGTCTGGTAGTCTGTCCCTCGTGCCC-3';

R335E$_{fwd}$,
(SEQ ID NO: 9)
5'-ACGAGGGACAGAATACCAGACATTTG-3';

R335E$_{rev}$,
(SEQ ID NO: 10)
5'-TGTCTGGTATTCTGTCCCTCGTGCCC-3';

R335F$_{fwd}$,
(SEQ ID NO: 11)
5'-ACGAGGGACATTCTACCAGACATTTGT-3';

R335F$_{rev}$,
(SEQ ID NO: 12)
5'-ATGTCTGGTAGAATGTCCCTCGTGCCC-3';

R335G$_{fwd}$,
(SEQ ID NO: 13)
5'-ACGAGGGACAGGATACCAGACATTT-3';

R335G$_{rev}$,
(SEQ ID NO: 14)
5'-GTCTGGTATCCTGTCCCTCGTGCCC-3';

R335K$_{fwd}$,
(SEQ ID NO: 15)
5'-CGAGGGACAAAATACCAGACATTTG-3';

R335K$_{rev}$,
(SEQ ID NO: 16)
5'-TGTCTGGTATTTTGTCCCTCGTGCC-3';

-continued

R335L_fwd,
(SEQ ID NO: 17)
5'-ACGAGGGACATTATACCAGACATTTGT-3';

R335L_rev,
(SEQ ID NO: 18)
5'-ATGTCTGGTATAATGTCCCTCGTGCCC-3';

R332G/R335E_fwd,
(SEQ ID NO: 19)
5'-ATATGGGGCAGGAGGGACAGAATACCAGACATTTG-3';

R332G/R335E_rev,
(SEQ ID NO: 20)
5'-TGTCTGGTATTCTGTCCCTCCTGCCCCATATATTA-3';

R332G/R335G_fwd,
(SEQ ID NO: 21)
5'-ATATGGGGCAGGAGGGACAGGATACCAGACATTT-3';

R332G/R335G_rev,
(SEQ ID NO: 22)
5'-GTCTGGTATCCTGTCCCTCCTGCCCCATATATTA-3';

as well as TRIM5$_{fwd}$ and TRIM5$_{rev}$.

Generation of Cells Stably Expressing TRIM5α Variants. Retroviral vectors encoding wild-type TRIM5α$_{hu}$, TRIM5α$_{rh}$ or mutants of TRIM5α$_{hu}$ proteins were created using pMIP vector. Recombinant viruses were produced by cotransfecting 293T cells in 6-well plates with 2 μg of the appropriate pMIP construct, 2 μg of pCL-Eco and 1 μg of pMD-G. Two days later, supernatants were collected, cleared by low-speed centrifugation and used immediately. TE671 and SUP-T1 cells were plated at 125,000 cells per well in 6-well plates. The next day, supernatants were replaced with 2 ml of MIP-TRIM5α retroviral vectors or with the empty parental vector MIP as a control. Two days post-transduction, cells were placed in medium containing 0.5 μg/ml of puromycin (EMD Biosciences). Selection was allowed to proceed for 1 week, even though untransduced control cells were killed in 2-3 days. Expression of the transduced TRIM5α was analyzed by western blotting, using antibodies directed against the FLAG epitope (mouse monoclonal; SIGMA®) or actin (rabbit polyclonal; Santa Cruz).

Viral Challenges.

For single-cycle infections of TE671 cells, 25,000 cells were seeded in 400 μl per well of 24-well plates. Cells were infected the next day with multiple doses of HIV-1$_{TRIP-CMV-GFP}$, MLV-N$_{GFP}$, MLV-B$_{GFP}$, SIV$_{mac-GFP}$, EIAV$_{GFP}$ or HIV-2$_{ROD-GFP}$. Two days postinfection, adherent cells were trypsinized and fixed in 1% formaldehyde-PBS while T cells were simply treated with formaldehyde. For HIV-1$_{NL-GFP}$ infections, SUP-T1 cells were plated at 200,000 cells in 400 μl per well of 24-well plates and infected with a single dose (150 μl) of virus. To avoid the initiation of a second cycle of replication, cells were fixed at 36 h. All cells were subjected to FACS analysis on a Cytomics™ FC 500 MPL instrument (BECKMAN COULTER®) using MXP/CXP™ software. Based on light scatter profiles, only intact cells were included in the analysis. GFP-positive cells were gated and counted as a percentage of total intact cells.

For spreading assays, 1.5×10$^6$ parental SUP-T1 cells were seeded in 2 ml of medium per well of 6-well plates. Cells were infected at low or high multiplicities of infection (M01) of HIV-1$_{NL4-3}$ (15 μl and 1.5 ml of virus, respectively). 20 h post-infection, cells were harvested by centrifugation at 1200 rpm for 5 min, washed once with culture medium, and resuspended in 1.5 ml of fresh medium. ~1.0×10$^5$ of these infected cells were mixed with 1.0×10$^6$ SUP-T1 cells expressing wild-type or mutant TRIM5α$_{hu}$ in 1 ml of medium per well of 12-well plates. Every 3 or 4 days, about two-thirds of each culture were harvested and cleared by centrifuging at 8000 rpm for 5 min in a microcentrifuge. Cultures were replenished with fresh medium while aliquots of cleared supernatant were preserved at −80° C. After four weeks, reverse transcriptase activity was quantified with the EnzChek™ Reverse Transcriptase Assay Kit (INVITROGEN®) according to the manufacturer's instructions and using serial dilutions of recombinant reverse transcriptase (provided by the NIH AIDS Reagents Program) as a standard. RT assays were performed in black clear bottom microtiter plates (CORNING®) which were read in a Synergy™ HT Multi-Mode microplate reader (BIO-TEK®) at an emission wavelength of 520 nm and excitation of 480 nm.

Example 2

Construction of the Human TRIM5α Mutant Library

Figure 1B:
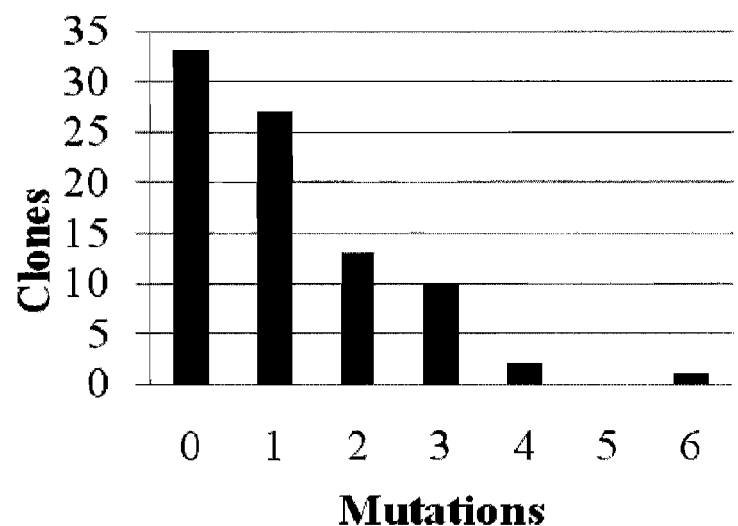
FIG. 1B shows the number of mutations per clone prior to functional screening. 86 clones were sequenced.
Figure 1C:
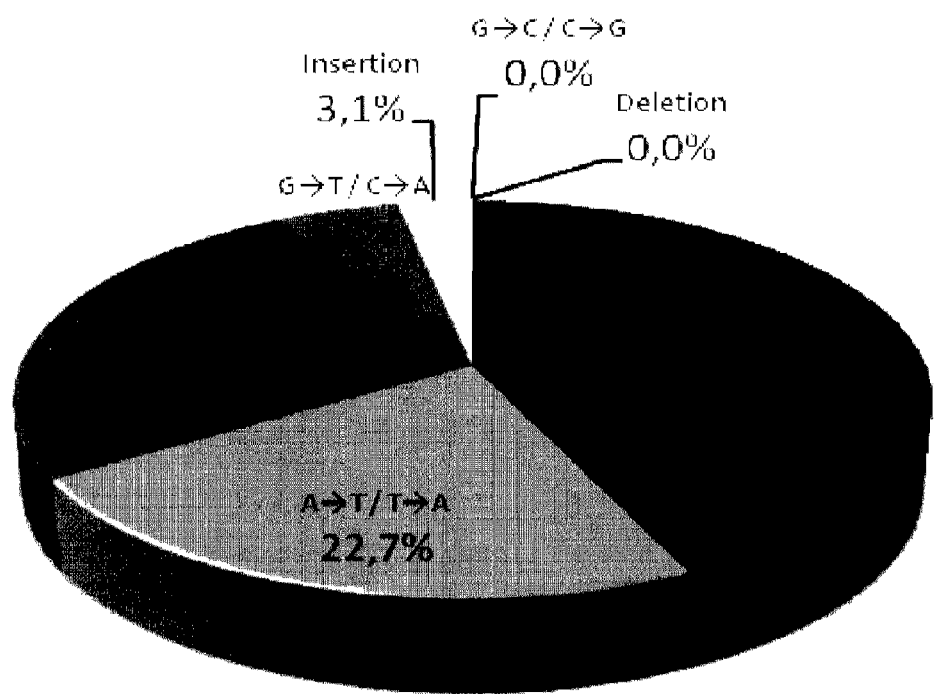
FIG. 1C shows an analysis of mutations found in the B30.2/SPRY domain of TRIM5α$_{hu}$. All 97 mutations found in the 86 clones analyzed were included.
Figure 1D:
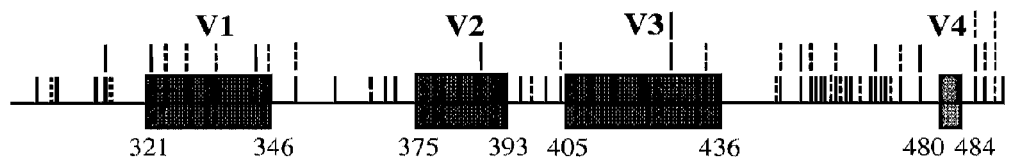
FIG. 1D shows the mapping of 94 substitutions along the TRIM5α$_{hu}$ B30.2/SPRY domain. Nonsilent substitutions are indicated with continuous lines while silent mutations are represented by dotted lines.
Figure 1E:
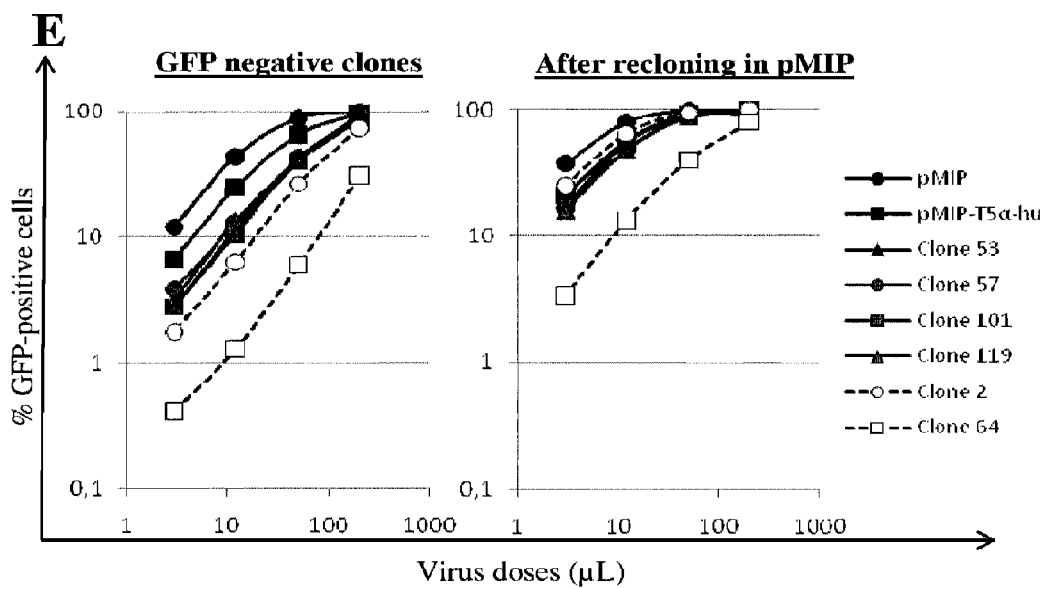
FIG. 1E shows a functional screen and isolation of a TRIM5α$_{hu}$ mutant that restricts HIV-1. Left panel: cell clones that were GFP-negative after exposure to a large amount of a GFP-expressing HIV-1 vector were infected with 4 different doses of HIV-1$_{TRIP-CMV-GFP}$. Control cells were transduced with wild-type TRIM5α$_{hu}$ or with the parental MIP vector. Shown are some of the clonal populations that displayed a 2-fold or more decrease in permissiveness to HIV-1 replication compared with the cells transduced with wild-type TRIM5α$_{hu}$. Right panel: TRIM5α$_{hu}$ cDNAs from these cell lines were recloned into pMIP and retransduced into parental TE671 cells. These cells and control cells were again challenged with the HIV-1 vector expressing GFP. Clone 64 contained the R335G mutation.

A human TRIM5α mutant library was constructed by error-prone PCR of the B30.2 domain (FIG. 1A). The frequency of mutations was within the desired range of 1-2 per clone (FIG. 1B). The mutations introduced were overwhelmingly (97%) substitutions, with a strong bias toward mutations at A/T residues (about 80%; see FIG. 1C), typical for this type of mutagenesis. Mutations were scattered all along the B30.2 domain of restriction (FIG. 1D). Some regions, like the first variable region and the region between v3 and v4, appeared to be mutational hot-spots, and this seems to correlate partly with their high A/T content. Among 94 substitution analyzed, 34 (36%) were silent and 17 (18%) were present more than once (eight were present twice, and one was present 3 times). Thus, enrichment for particular point mutations, a recurring problem in PCR-based random mutagenesis, was relatively low in this screen by virtue of the PCR conditions used (high amount of template DNA, low number of cycles). No mutations were found in TRIM5α$_h$, regions upstream of the B30.2 domain. The library was retrovirally transduced into human TE671 cells. Untransduced cells were eliminated by puromycin treatment. Functional screening was done by infecting the library-expressing cells with large doses (typically leading to 99% infected cells) of an HIV-1 vector expressing GFP (HIV-1$_{TRIP-CMV-GFP}$) then isolating cells that were GFP-negative and thus putatively resistant to HIV-1 infection. This approach is the same as the one described in Stremlau et al. (Stremlau M. et al., 2004. Nature 427:848-53). In a second step of functional selection, 108 GFP-negative cell clones were infected with 4 doses of the GFP-expressing HIV-1 vector, along with the control cells transduced with wild-type TRIM5α$_{hu}$ or with the empty expression construct (pMIP). 40 of the clonal cell lines were found to show a 2-fold or more decrease in permissiveness to HIV-1 infection compared to cells transduced with wild-type TRIM5α$_{hu}$ (some examples are shown in FIG. 1E). In a third step, transgenic TRIM5α$_{hu}$ cDNAs were PCR-amplified from all of these clones and re-introduced into naïve TE671 cells by retroviral transduction using the same MIP vector. These cells were again challenged with 4 doses of HIV-1$_{TRIP-CMV-GFP}$, and it was found that only one cell line (clone 64) showed significant resistance to HIV-1 (FIG. 1E). Therefore, it appears that the resistance to HIV-1 infection observed in the other 39 clonal cell lines from step two of functional screening was due to factors other than the expression of exogenous TRIM5α.

Transgenic TRIM5α in clone 64 contained the A1003G mutation (an adenine to guanine substitution at position 1003 in the human TRIM5α cDNA), resulting in an arginine to glycine substitution at position 335 of the human TRIM5α protein. It also had a silent mutation (A906C). Arg335 is located in the hypervariable region v1 of the B30.2 domain.

Example 3

Figure 2A:
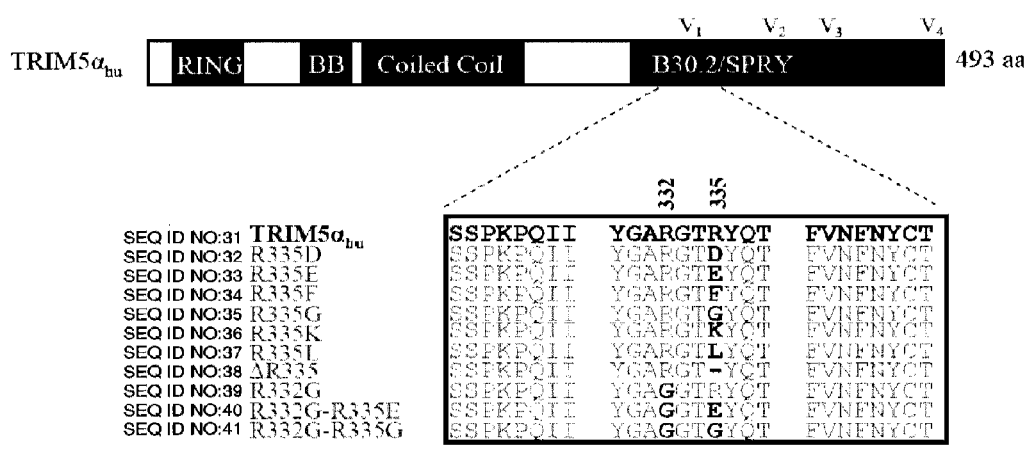
FIG. 2A shows the main regions of TRIM5α$_{hu}$, with the mutations introduced in the first variable region (v1) of the B30.2/SPRY domain of TRIM5α$_{hu}$ indicated in bold.
Figure 2B:
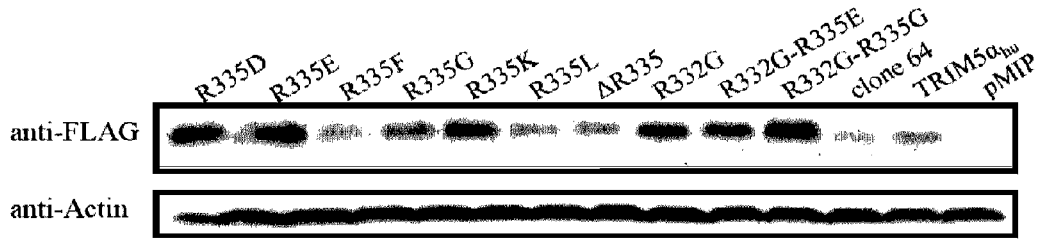
FIG. 2B shows the expression of FLAG-tagged wild-type and mutant TRIM5α$_{hu}$ in transduced TE671 cells was assessed by western blotting using antibodies directed against the FLAG epitope (top panel) or actin (bottom panel)
Figure 3A:
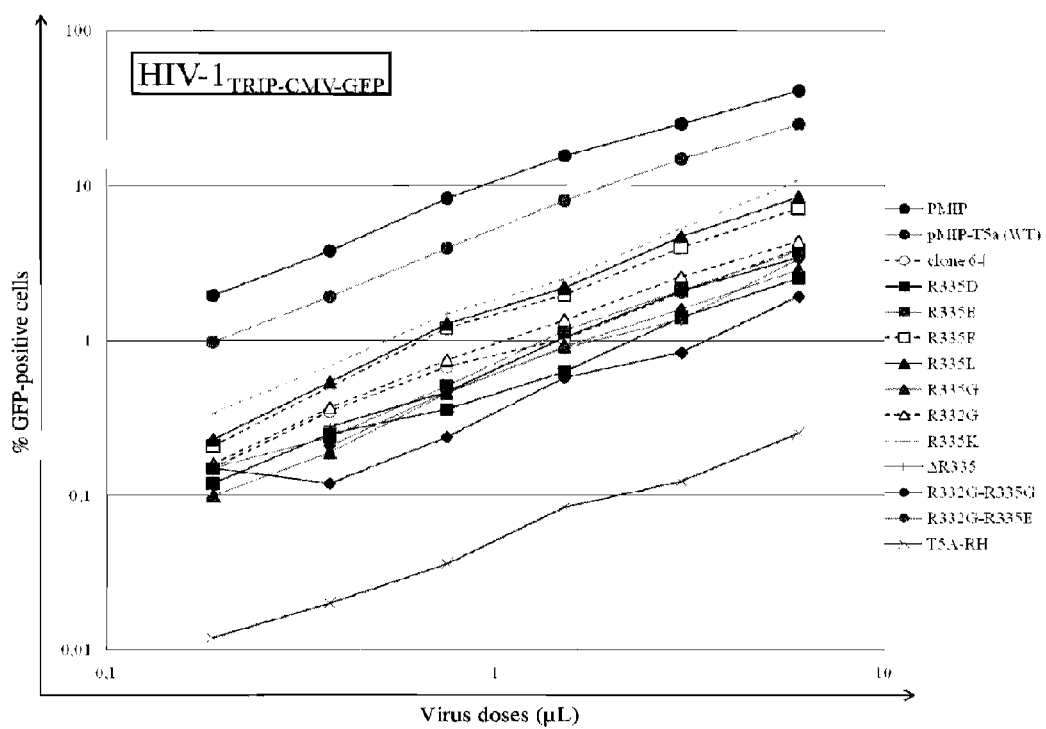
FIGS. 3A to 3F show the percentages of GFP-positive cells following challenge with HIV-1$_{TRIP-CMV-GFP}$, HIV-2$_{ROD-GFP}$, SIV$_{MAC-GFP}$, EIAV$_{GFP}$, N-MLV$_{GFP}$ and B-MLV$_{GFP}$, respectively. Black circles=PMIP; grey circles=PMIP-T5a (WT); white circles=clone 64; black squares=R335D; grey squares=R335E; white squares=R335F; black triangles=R335L; grey triangles=R335G; white triangles=R332G; grey crosses=R335K; black crosses=ΔR332; black diamonds=R332G-R335G; grey diamonds=R332G-R335E.
Figure 3B:
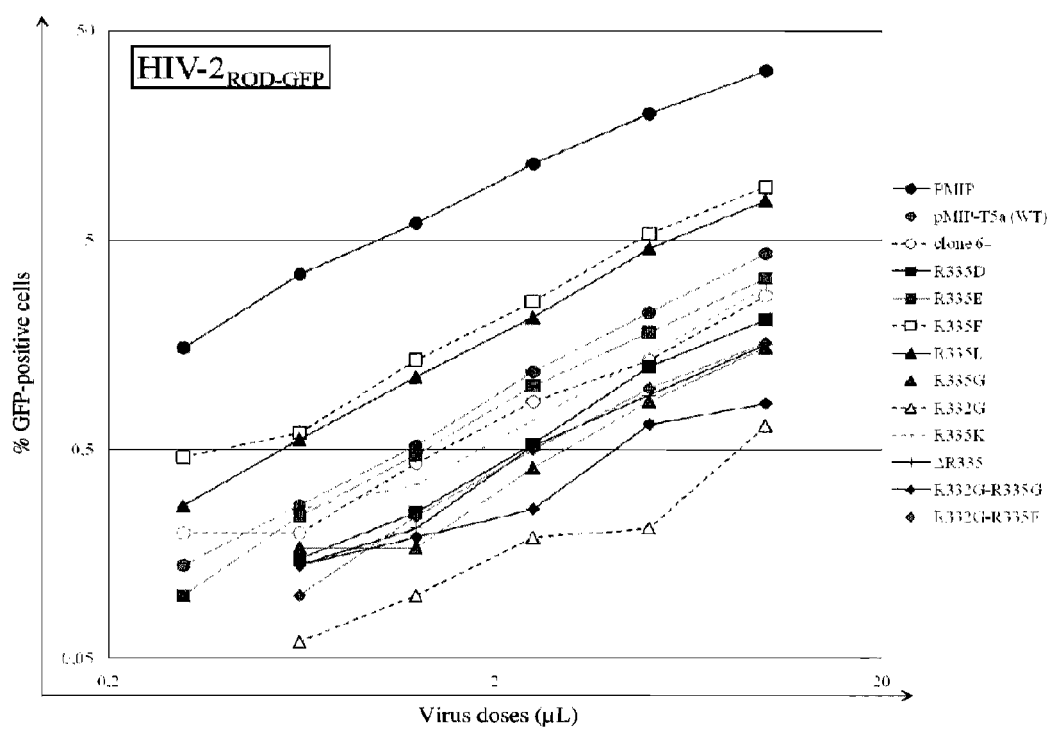
Figure 3C:
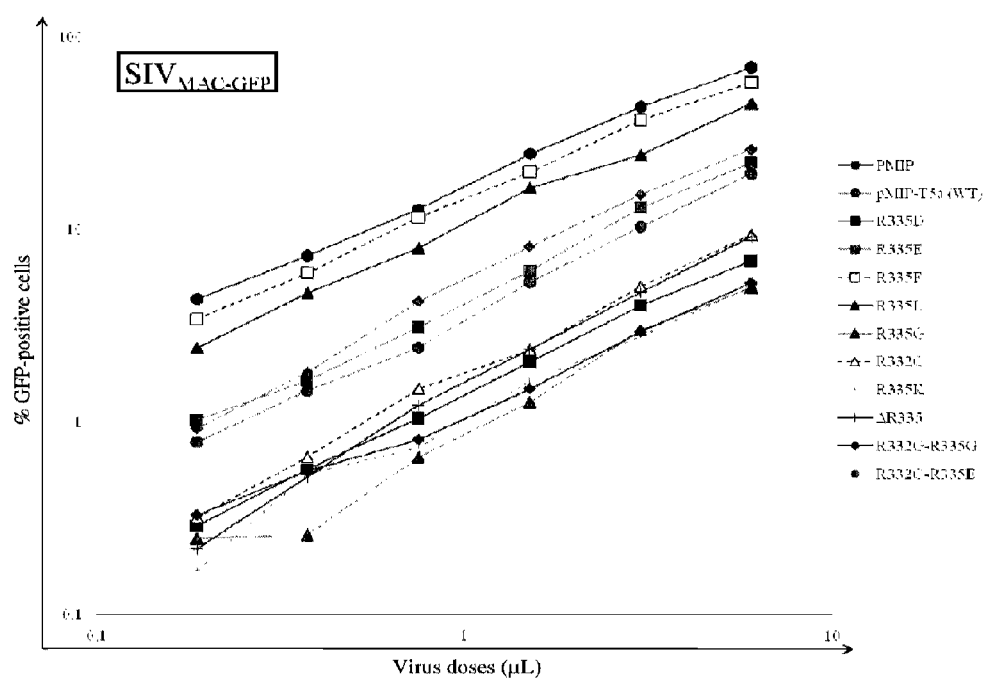
Figure 3D:
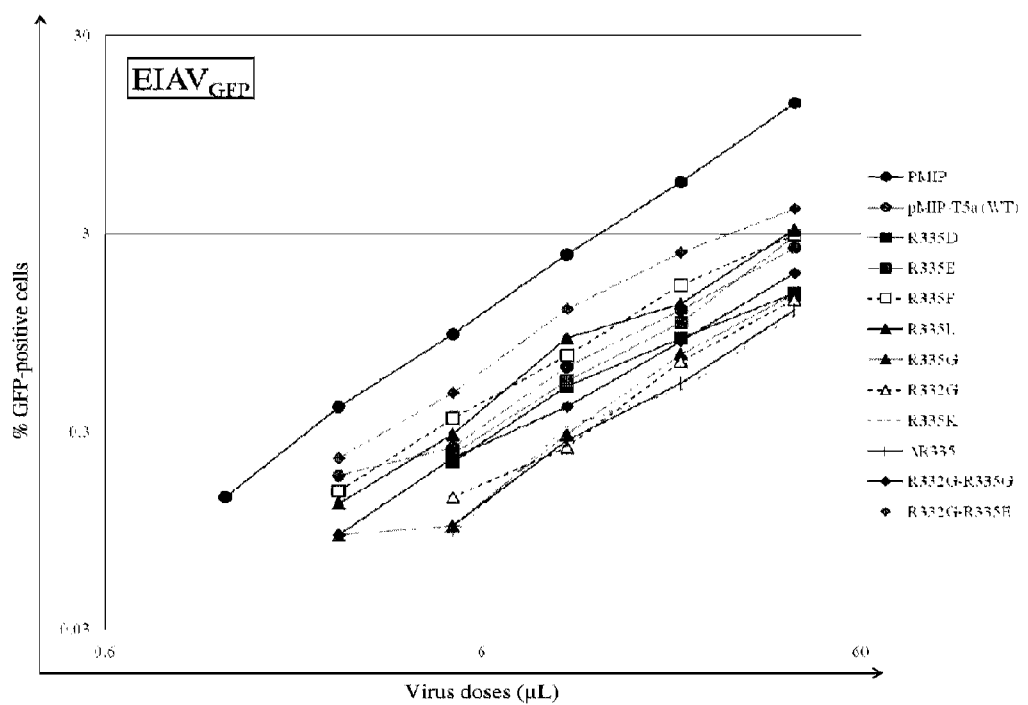
Figure 3E:
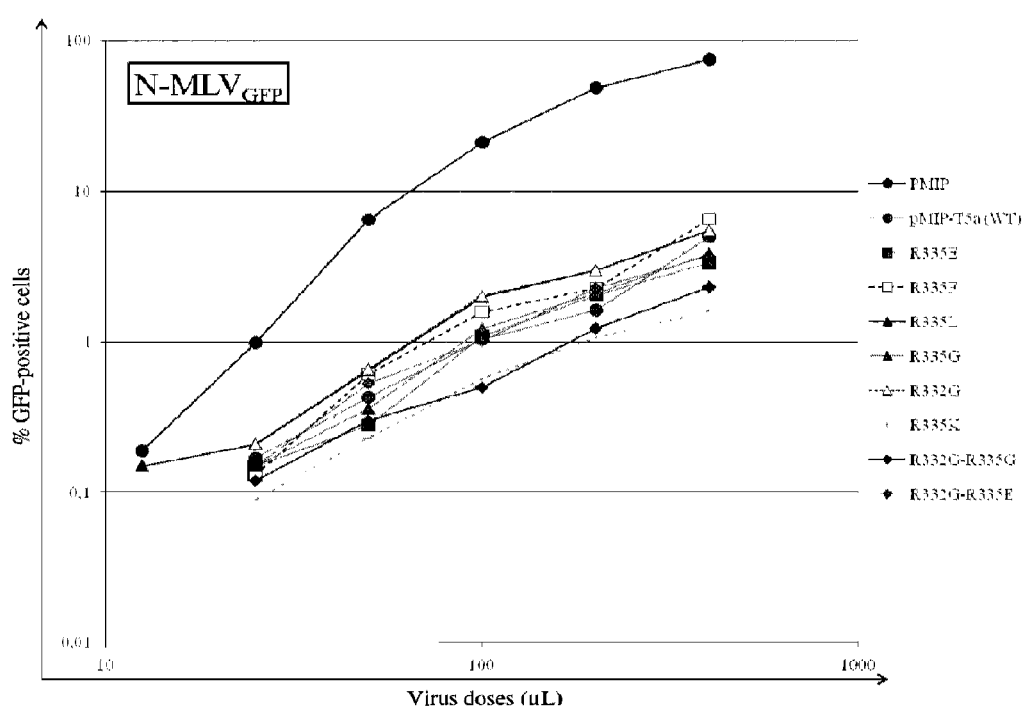
Figure 3F:
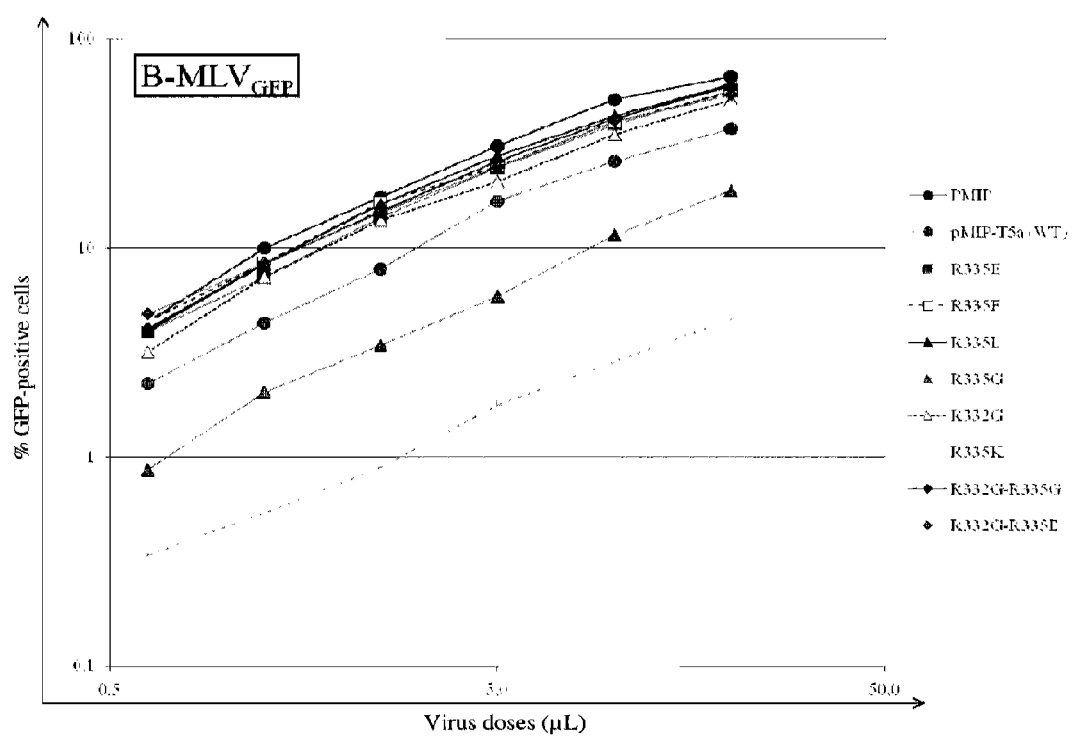

Mutation of the Arginine Residues at Position 332 and/or 335 Affects TRIM5α$_{Hu}$-Mediated Lentivirus Restriction In order to explore the role of the arginine residues at positions 332 and 335 in the restriction range of TRIM5α$_{hu}$, a series of single mutants having amino acids substitutions at position 335, and double mutants having substitutions at positions 332 and 335, were generated (FIG. 2A). First, to insure that R335G was the sole mutation in clone 64 causing the observed phenotypical change, the mutation was reintroduced in the parental plasmid. To investigate the possibility that increased restriction of HIV-1 was caused by a suppression of the positive charge at position 335, an arginine-to-lysine mutant (R335K) was also generated. Mutants having the basic-to-acidic mutations R335D and R335E were also constructed, as well as mutants in which R335 was replaced by hydrophobic residues, namely the aromatic phenylalanine (R335F) and the aliphatic leucine (R335L). An additional mutant lacking the Arg335 residue (ΔR335) was generated. Finally, the following mutants/double mutants were constructed: R332G, R332G/R335G and R332G/R335E. All mutated TRIM5α$_{hu}$ were transduced into TE671 cells and into the lymphocytic T cell line SUP-T1, and expression was assessed by western blotting using an antibody recognizing the C-terminal FLAG tag. Among other similarly FLAG-tagged TRIM5α orthologues, the human version is notoriously difficult to detect. In fact, no signal for this protein is seen in western blots from two previously published studies. By optimizing the experimental conditions, we were able to detect all TRIM5α$_h$ mutants in TE671 cells (but not in SUP-T1) and all of them were found to migrate at the expected molecular weight (FIG. 2B). Levels of expression seemed to vary between mutants, but this could be partly due to the nonlinear nature of the signal at such low efficiency of detection.

All the cell lines generated were challenged with retroviral vectors derived from HIV-1, from other lentiviruses (HIV-2, simian immunodeficiency virus macaque strain 239, equine infectious anemia virus) and from the simpler retrovirus murine leukemia virus (FIG. 3 and Table 1). The N-MLV and B-MLV Gag proteins differ by a few amino acids (Bock, M. et al., 2000. J Virol 74:7422-30), and amino acid 110 in the capsid domain determines the sensitivity of MLV to TRIM5α$_h$, and to Fv1, another restriction factor functionally (if not structurally) related to TRIM5α(Passerini, L. D. et al., 2006. J Virol 80:2100-5, Towers, G. et al. 2000. Proc Natl Acad Sci USA 97:12295-9). N-MLV is targeted by TRIM5α$_{hu}$ while B-MLV is not. All retroviral vectors expressed the enhanced GFP which thus served as a marker to quantitate the percentage of infected cells.

Overexpression of wild-type TRIM5α$_{hu}$ slightly inhibited HIV-1 infection (less than 2-fold). All mutants caused a significant decrease in permissiveness to HIV-1 (FIG. 3, top left panel, and Table 1). R332G and R335G both restricted HIV-1 by 10- to 20-fold. Clone 64 cDNA-expressed TRIM5α$_{hu}$ also inhibited HIV-1 to the same extent, confirming that R335G was the only mutation in clone 64 having a role in the restriction. All other mutations decreased HIV-1 infection by at least 6-fold and by up to 35-fold, the mutant with the strongest effect being the double substitution R332G/R335G.

As also shown FIG. 3 and Table 1, HIV-2 was significantly inhibited (10-fold) by overexpression of TRIM5α$_{hu}$. R332G caused an even greater (60-fold) inhibition of this virus, while R335L and R335F restricted HIV-2 only weakly. All other mutants had an HIV-2 restriction phenotype intermediate between wild-type TRIM5α$_{hu}$ and the R332G mutant. Wild-type TRIM5α$_{hu}$ weakly inhibited SIV$_{mac}$239 (5-fold), and this restriction was abolished by introducing hydrophobic residues at position 335. A group of mutations that included R332G, R335G and the deletion of Arg335 decreased SIV-mac239 replication by 10- to 20-fold, while R335E and the double mutation R332G/R335E had a more moderate effect. Thus, arginine 332 and 335 modulate the restriction of not only HIV-1 but also of other primate lentiviruses.

The effect of the constructs on the replication of EIAV and N-MLV, two viruses that are efficiently restricted by the human endogenous TRIM5α, was also tested. Overexpression of wild-type TRIM5α$_{hu}$ inhibited both types of retroviral vectors. For N-MLV, the inhibition was greater at relatively high doses of viral input (e.g., 100 μl of virus) than at lower doses such as 25 μl. This is likely due to the effect of saturation of the restriction at high virus doses (Cowan, S., et al., 2002. Proc Natl Acad Sci USA 99:11914-9; Towers, G., et al., 2000. Proc Natl Acad Sci USA 97:12295-9): endogenous TRIM5α$_h$ is saturated by large amounts of incoming N-MLV capsids but overexpression of TRIM5α$_h$ restores restriction. EIAV replication was decreased by 5-fold by wild-type TRIM5α$_{hu}$. Several mutations (R332G, R335K, ΔR335) inhibited EIAV at significantly higher levels (up to 12-fold) while the double mutation R332G/R335G had a smaller effect (3-fold). Thus, arginine residues at positions 332 and 335 are also involved in the restriction of nonsimian lentiviruses.

Mutations at positions 332 and 335 had more modest effects on the restriction of the retrovirus N-MLV by TRIM5α$_{hu}$ (FIG. 3 and Table 1). For instance, in conditions in which TRIM5α$_h$ inhibited N-MLV infection in cells by 20- to 30-fold, some mutations (R335K, R332G/R335G) increased that inhibition by about 2-fold, while others decreased it by about 2-fold. Infection with a B-MLV vector was only marginally affected by most mutations at the two arginine residues, with the exception of R335G and R335K, which inhibited this virus by about 5-fold and 20-fold, respectively. All the other mutants behaved like the mock-transduced cells. These data show that Arg335 also influences the sensitivity of N-MLV and B-MLV to the restriction by TRIM5α$_{hu}$, but in a manner different from what is seen with lentiviruses: (i) unlike that of lentiviruses, restriction of N-MLV is not significantly affected by the introduction of hydrophobic residues at position 335; (ii) B-MLV is the only virus analyzed here that is specifically inhibited by the R335K mutation (i.e., R335K is the only mutant analyzed that significantly inhibits B-MLV).

TABLE 1

Restriction of selected retroviruses by TRIM5α$_{hu}$ mutants[a]

| TRIM5α$_{hu}$ variant | Restriction of: | | | | | |
|---|---|---|---|---|---|---|
| | HIV-1 | HIV-2 | SIV$_{mac}$ | EIAV | N-MLV | B-MLV |
| Wild-type | + | ++ | ++ | ++ | +++ | + |
| R335D | ++++ | ++++ | +++ | ++ | ND | ND |
| R335E | +++ | +++ | + | + | ++++ | − |
| R335L | ++ | ++ | − | + | +++ | − |
| R335F | ++ | + | − | + | +++ | − |
| R335G | +++ | ++++ | +++ | ++ | +++ | + |

TABLE 1-continued

Restriction of selected retroviruses by TRIM5α$_{hu}$ mutants[a]

| TRIM5α$_{hu}$ variant | Restriction of: | | | | | |
|---|---|---|---|---|---|---|
| | HIV-1 | HIV-2 | SIV$_{mac}$ | EIAV | N-MLV | B-MLV |
| R332G | +++ | ++++ | ++ | ++ | ++ | − |
| R335K | ++ | +++ | +++ | +++ | ++++ | +++ |
| ΔR335 | +++ | ++++ | +++ | +++ | ND | ND |
| R332G/R335G | ++++ | ++++ | +++ | ++ | ++++ | − |
| R332G/R335E | +++ | ++++ | + | + | +++ | − |

[a]Decrease in permissiveness to retroviral transduction by GFP-expressing vectors derived from the indicated retroviruses, relative to mock-transduced control cells. Cell lines expressing wild-type or mutated TRIM5α$_{hu}$ were infected with the retroviral vectors at a dose leading to about 10% infected cells for the mock-transduced control. The percentages of infected cells were determined 2 days later by flow cytometry. −, less than 2-fold decrease; +, 2- to 5-fold decrease; ++, 5- to 10-fold decrease; +++, 10- to 20-fold decrease; ++++, >20-fold decrease. ND, not determined.

Figure 4A:
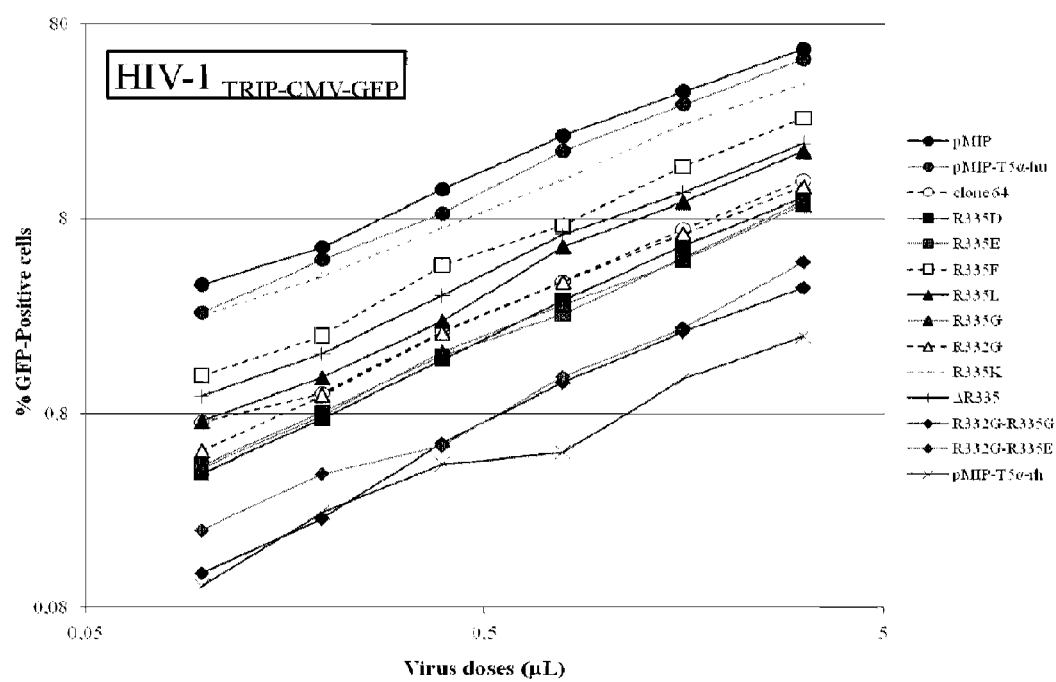
FIG. 4 shows HIV-1 restriction in a T lymphocyte cell line. SUP-T1 cells expressing wild-type or mutant TRIM5α$_h$, were challenged with multiple doses of the VSV G-pseudotyped, multiply attenuated HIV-1$_{TRIP-CMV-GFP}$ vector (FIG. 4A) or with a single dose of HIV-1$_{NL-GFP}$, a non-pseudotyped NL4-3-derived vector in which only the Nef protein has been deleted and replaced by GFP (FIG. 4B). The percentages of GFP-positive cells were determined by flow cytometry after 48 h (FIG. 4A) or 36 h (FIG. 4B). Error bars in FIG. 4B are standard deviations from quadruplicate infections.
Figure 4B:
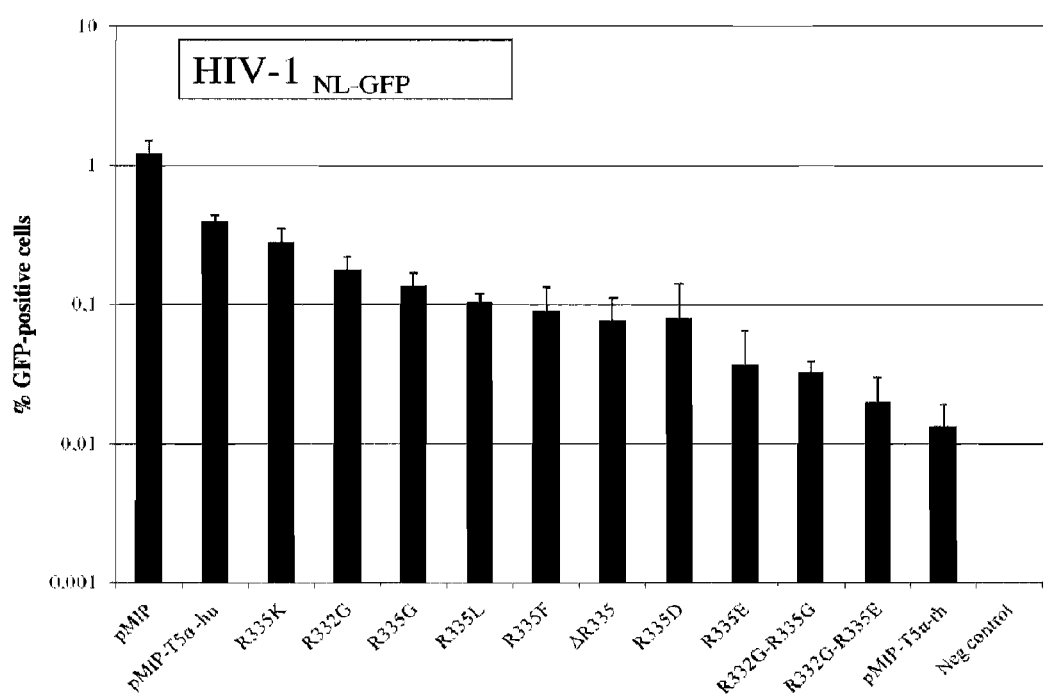
Figure 5A:
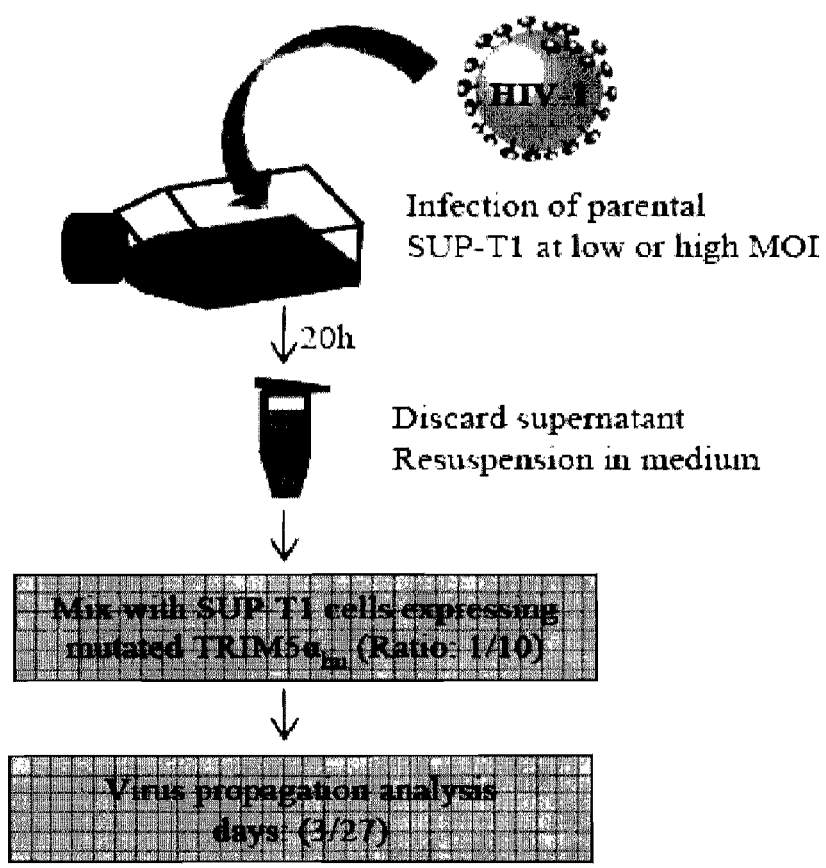
FIG. 5A depicts an overview of the protocol used. Parental SUP-T1 cells were infected with relatively low or high doses of HIV-1$_{NL4-3}$. 20 h later, the cells were mixed with SUP-T1 cells expressing wild-type or mutated TRIM5α$_{hu}$ at a 1:10 ratio.
Figure 5B:
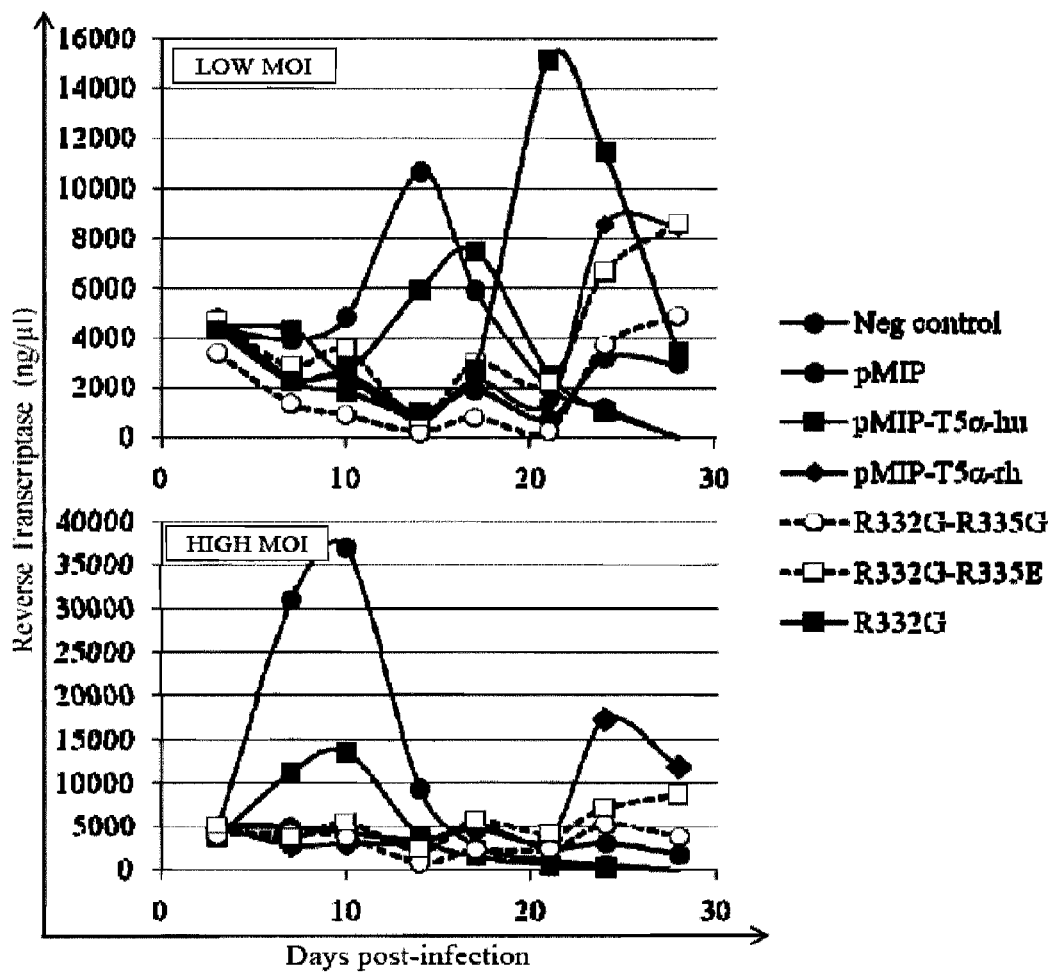
FIG. 5B shows the reverse transcriptase activity measured every 3 to 4 days for 28 days. Reverse transcriptase was quantified using a fluorescence-based kit and using dilutions of pure recombinant reverse transcriptase as a standard. "Neg control" indicates uninfected parental cells.

The level of protection conferred by TRIM5α$_{hu}$ mutants was analyzed in the SUP-T1 T cell line. These cells were transduced with the various TRIM5α$_{hu}$ constructs, and untransduced cells were eliminated by puromycin treatment. As shown FIG. 4A, these cells were first challenged with the same HIV-1-derived vector (HIV-1$_{TRIPCMV-GFP}$) that had been used in TE671 cells. TRIM5α$_{rh}$ caused a decrease in permissiveness to HIV-1 of about 25-fold, thus significantly smaller than what is typically found in fibroblasts (100-fold or more). R332G and R335G both inhibited HIV-1 by about 8-fold, while R335K had no restrictive effect at all. Overall, mutants showed phenotypes similar to what had been found in TE671 cells. The two double-mutants restricted HIV-1 to nearly TRIM5α$_{rh}$ levels, confirming that the mutations had combined effects.

The protection conferred by TRIM5α$_{hu}$ mutants was assessed using the SUP-T1 cell lines with a version of the infectious HIV-1 clone NL4-3 expressing GFP in place of Nef. This virus enters the cells by virtue of its own envelope proteins instead of being pseudotyped with VSV-G. All but one of the viral proteins are encoded and expression of GFP allows the quantification of cells' permissiveness to HIV-1$_{NL-GFP}$ in a fashion similar to HIV-1$_{TRIM-CMV-GFP}$. In this system, a group of mutants that included R335G, R335L, R335F, ΔR335 and R335D all decreased HIV-1 replication by about 10-fold, while R332G had a slightly smaller effect. Again, the two double-mutants inhibited HIV-1 the most efficiently (about 50-fold) and were nearly as restrictive as TRIM5α$_{rh}$.

Example 4

Figure 8B:
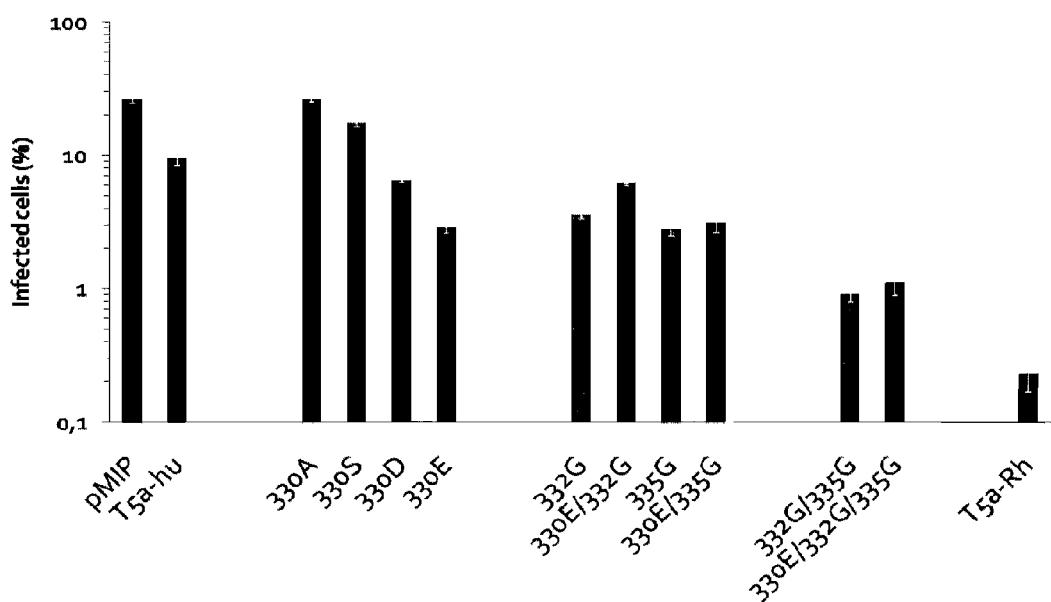

Mutation of the Arginine Residues at Position 332 and 335 Affects TRIM5α$_{hu}$ Mediated HIV-1 Propagation Over Multiple Replication Cycles The inhibition of HIV-1 propagation by the double-mutants upon multiple replication cycles was next tested. It has been recently shown that in in vitro T cell cultures, and probably in most instances in vivo, HIV-1 is transmitted from one cell to the next through virological synapses (Groot, F. et al., 2008. *Blood* 111:4660-3; Haller, C., and O. T. Fackler. 2008. *Biol Chem* 389:1253-60; Rudnicka, D. et al., 2009. *J Virol* 83:6234-46) rather than via cell-free particles. This mode of transmission may result in different sensitivities of the incoming viruses to TRIM5α. It may also result in TRIM5α targeting susceptible retroviruses not just at post-entry stages but also at later stages of the retroviral life cycle (Richardson, M. W. et al., 2008. *J Virol* 82:11117-28). The potency of the R332/R335 double-mutants in the context of cell to cell transmissions was determined. "Classical" virus spreading assays are initiated by adding cell-free virus on a culture of T cells. Under these conditions, the first round of entry events is thus mechanistically different from subsequent rounds. In order to assay virus spread in more consistent conditions, parental SUP-T1 cells were infected with HIV-$1_{NL4-3}$ at low or high multiplicity of infections (MOIs). The next day, these cells were washed and then placed in culture at a ratio of 1:10 with the SUP-T1 cells expressing wild-type TRIM5$\alpha_{hu}$, mutant TRIM5$\alpha_{hu}$ or TRIM5$\alpha_{rh}$ (FIG. 5A). Reverse transcriptase activity was measured in the supernatants of infected cells for 4 weeks following the initiation of the co-cultures. At low MOI (FIG. 5B, upper panel), viral replication peaked after 14 days of virus spread in control (mock-transduced) cells. HIV-1 replication in cells expressing exogenous TRIM5$\alpha_{hu}$ was slightly delayed, consistent with the small inhibition effect seen in other experimental settings. Spreading infections in cells expressing TRIM5$\alpha_{rh}$, R332G/R335G and R332G/R335E TRIM5$\alpha_{hu}$ were all strongly delayed since no reverse transcriptase activity could be detected prior to day 24. The single-mutant R332G also caused a significant delay in replication (one week), but the inhibition was weaker as compared to the double-mutants. At a higher MOI (FIG. 5B, bottom panel), viral replication reached its peak earlier (10 days) in mock-transduced cells or in cells transduced with TRIM5$\alpha_{hu}$, and the small restriction effect observed at low MOI with TRIM5$\alpha_{hu}$ overexpression was abolished. Also, replication in cells expressing the two double-mutants or expressing TRIM5$\alpha_{rh}$, was perhaps even more strongly delayed than at low MOI (approximately 14 versus 10 days).

Example 5

Mutation of the Glycine Residue at Position 330 Affects TRIM5$\alpha_{hu}$-Mediated Lentivirus Restriction Additional mutagenic screens were performed to generate novel variants of TRIM5$\alpha_{hu}$ with HIV-1 restriction activity. Degenerated oligonucleotides were used and mutagenesis was limited to the first variable loop of the PRYSPRY domain. Specifically, TRIM5$\alpha_{hu}$ was submitted to PCR-mediated mutagenesis using a degenerated oligoDNA (v1mut) to introduce mutations in the v1 region. The sequence of the v1mut oligoDNA was: aga caa gtg agc tct CCg AAa CCa CAg ATa ATa TAt GGg GCa CGa GGg ACa AGa TAc CAg ACa TTt GTg AAt ttc aat tat tgt act (SEQ ID NO: 29). The 38 residues in capital letters are the ones that were selected for variation during the production of the oligoDNA at SIGMA-GENOSYS®. They span positions 967-1023 of the published TRIM5$\alpha_{hu}$ coding sequence (SEQ ID NO: 23), corresponding to the 323-341 region (PKPQIIYGARGTRYQTFVN) of the expected TRIM5$\alpha_{hu}$ translation product (SEQ ID NO:24). A 5% mutation rate at each of these 38 residues was requested.

The PCR products were ligated into the retroviral vector pMIP-TRIM5$\alpha_{hu}$ plasmid DNA, the same backbone vector used to construct the human TRIM5α mutant library described above. A 3,600 clones-rich pooled DNA library was constructed. This DNA was used to produce MIP-based retroviral vectors, similarly to what is described above. Human TE671 cells were transduced with the library and untransduced cells were eliminated. The transduced cells were subsequently challenged with a large dose of an HIV-1 vector expressing GFP. GFP-negative cells, potentially resistant to HIV-1, were isolated. Among these, 5 contained a mutated version of TRIM5$\alpha_{hu}$ that did confer partial resistance (about ten-fold) against HIV-1, as evidenced by recloning into TE671 cells. These 5 variants contained the mutations: Clone B1, P325U1328T/R332G/Q337E/T338P/Q337E; Clone B3, K324Q/Y336C/T338P; D3, P325/I328T/R332G/T334A/Q337E/T338P; E4, R332/Q337E; G4, I328S/Y329C/G330E/G333V/Q337V. Resistance against HIV-1 was explained in 3 of these 5 clones (B1, D3 and E4) by the presence of mutations at position 332. Resistance in the other two clones (B3 and G4) could be theoretically attributed to single mutations or to combinations of mutations.

pMIP-TRIM5α$_h$ variants containing either one of each of the 8 mutations from clones B3 and G4 were constructed. TE671 cells were transduced with these constructions, and permissiveness to an HIV-1 vector carrying the GFP gene was tested as previously described. The results of this experiment are shown in FIG. 8A. As can be seen, mutation G330E from clone G4 was the most restrictive, conferring a ~10-fold resistance to HIV-1, similar to that conferred by the R332G mutation. Mutation Y336C from clone B3 conferred a ~4-fold resistance to HIV-1, whereas mutations K324Q, Q337P, 1328S and G333V conferred a resistance of about 2- to 3-fold. Other substitutions at position 330 were tested (G330A, G330S and G330D), as shown in FIG. 8B. Also, results from experiments in which the effect on HIV-1 restriction of mutation G330E combined with mutations at positions 332 and/or 335 are depicted in FIG. 8B.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A recombinant mutant tripartite motif-containing 5 alpha (TRIM5α) polypeptide conferring a higher resistance to a lentivirus infection relative to wild-type human TRIM5α, said mutant TRIM5α polypeptide comprising an arginine to glycine substitution at an amino acid corresponding to amino acid 335 of wild-type human TRIM5α.

2. The mutant TRIM5α polypeptide of claim 1, comprising a further mutation at an amino acid corresponding to amino acid 332 of wild-type human TRIM5α.

3. The mutant TRIM5α polypeptide of claim 2, wherein said further mutation is a substitution with a Gly residue.

4. The mutant TRIM5α polypeptide of claim 1, wherein said mutant TRIM5α polypeptide comprises: (i) a Gly to Glu substitution at an amino acid corresponding to amino acid 330 of wild-type human TRIM5α; (ii) an Arg to Gly substitution at an amino acid corresponding to amino acid 332 of wild-type human TRIM5α; and (iii) an Arg to Gly substitution at an amino acid corresponding to amino acid 335 of wild-type human TRIM5α.

5. The mutant TRIM5α polypeptide of claim 1, wherein said lentivirus infection is human immunodeficiency infection (HIV).

6. A recombinant nucleic acid encoding the mutant TRIM5α polypeptide of claim 1.

7. A vector comprising the nucleic acid of claim 6.

8. A cell comprising the mutant TRIM5α polypeptide of claim 1.

9. A composition comprising the mutant TRIM5α polypeptide of claim 1 and a pharmaceutically acceptable carrier.

10. A cell comprising the nucleic acid of claim 6.

11. The mutant TRIM5α polypeptide of claim 1, which further comprises a mutation at an amino acid corresponding to amino acid 324, 328, 333, 336, 337 or 338 of wild-type human TRIM5α.

* * * * *